United States Patent
Bonventre et al.

(10) Patent No.: US 9,651,561 B2
(45) Date of Patent: May 16, 2017

(54) DIAGNOSIS AND TREATMENT OF ENDOMETRIOSIS AND RELATED CONDITIONS

(71) Applicant: THE BRIGHAM AND WOMEN'S HOSPITAL, INC., Boston, MA (US)

(72) Inventors: Joseph V. Bonventre, Wayland, MA (US); Venkata Sabbisetti, Brighton, MA (US)

(73) Assignee: The Brigham and Womens's Hospital, Inc., Boston, MA (US)

( * ) Notice: Subject to any disclaimer, the term of this patent is extended or adjusted under 35 U.S.C. 154(b) by 0 days.

(21) Appl. No.: 14/443,804

(22) PCT Filed: Nov. 13, 2013

(86) PCT No.: PCT/US2013/069880
§ 371 (c)(1),
(2) Date: May 19, 2015

(87) PCT Pub. No.: WO2014/081598
PCT Pub. Date: May 30, 2014

(65) Prior Publication Data
US 2015/0293114 A1    Oct. 15, 2015

Related U.S. Application Data

(60) Provisional application No. 61/728,413, filed on Nov. 20, 2012.

(51) Int. Cl.
| | |
|---|---|
| G01N 33/68 | (2006.01) |
| A61B 1/313 | (2006.01) |
| A61K 31/522 | (2006.01) |
| A61K 31/567 | (2006.01) |
| A61K 31/57 | (2006.01) |
| A61K 31/58 | (2006.01) |
| A61K 38/09 | (2006.01) |
| A61K 38/00 | (2006.01) |

(52) U.S. Cl.
CPC .......... *G01N 33/689* (2013.01); *A61B 1/3132* (2013.01); *A61K 31/522* (2013.01); *A61K 31/567* (2013.01); *A61K 31/57* (2013.01); *A61K 31/58* (2013.01); *A61K 38/09* (2013.01); *A61K 38/00* (2013.01); *G01N 2800/364* (2013.01); *G01N 2800/52* (2013.01)

(58) Field of Classification Search
None
See application file for complete search history.

(56) References Cited

U.S. PATENT DOCUMENTS

| | | |
|---|---|---|
| 2011/0045002 A1 | 2/2011 | Kuchroo et al. |
| 2011/0287964 A1 | 11/2011 | Bonventre et al. |

OTHER PUBLICATIONS

Sangoi et al., Laboratory Investigation, (Feb. 2010) vol. 90, Supp. Suppl. 1, pp. 216A-217A. Abstract No. 966.*
Han et al., Kidney International, 2002; 62: 237-244.*
Veras et al., Am J Surg Pathol. 2009; 33: 844-853.*
The abstract by Thompson (from J Clin Endocrinol Metab. 1991; 72: 1036-41); abstract only.*
The web article published Mar. 6, 2011, available at dhinfo.org/2011/03/tests-used-to-diagnose-endometriosis/.*
Waikar et al., Kidney International; 2010: 78, 486-494; doi:10.1038/ki.2010.165; published online Jun. 16, 2010.*
Lin et al., "Human Kidney Injury Molecule-1 (hKIM-1): A Useful Immunohistochemical Marker for Diagnosing Renal Cell Carcinoma and Ovarian Clear Cell Carcinoma", Am. J. Surg. Pathol., vol. 31, No. 3, pp. 371-381 (2007).
Peresada, "Endometrios: diagnosticheskie, klinicheskie, onkologicheskie I lichebnye aspekty." Medistynski novosti. 14:15-26 (2009). [English translation].

* cited by examiner

*Primary Examiner* — Christina Borgeest
(74) *Attorney, Agent, or Firm* — Nixon Peabody LLP

(57) ABSTRACT

The technology described herein relates to KIM-1 and the diagnosis, prognosis, and treatment of endometrial diseases and disorders.

7 Claims, 9 Drawing Sheets

DIAGNOSIS AND TREATMENT OF ENDOMETRIOSIS AND RELATED CONDITIONS

CROSS-REFERENCE TO RELATED APPLICATIONS

This application is a 35 U.S.C. §371 National Phase Entry Application of International Application No. PCT/US2013/069880 filed Nov. 13, 2013, which designates the U.S., and which claims benefit under 35 U.S.C. §119(e) of U.S. Provisional Application No. 61/728,413 filed Nov. 20, 2012 the contents of which are incorporated herein by reference in their entirety.

GOVERNMENT SUPPORT

This invention was made with government support under Grant No. DK072381 awarded by the National Institutes of Health. The U.S. government has certain rights in the invention.

SEQUENCE LISTING

The instant application contains a Sequence Listing which has been submitted electronically in ASCII format and is hereby incorporated by reference in its entirety. Said ASCII copy, created on Nov. 13, 2013, is named 043214-075081-PCT_SL.txt and is 9,815 bytes in size.

TECHNICAL FIELD

The technology described herein relates to the diagnosis and treatment of endometriosis-related conditions (e.g. endometriosis and ovarian clear cell adenocarcinoma) as well as methods of reducing angiogenesis.

BACKGROUND

Currently, serum CA-125 is the gold standard clinical marker for the diagnosis of all subtypes of epithelial ovarian carcinoma (EOC). However, serum CA-125 exhibits poor sensitivity, particularly in detecting clear cell ovarian carcinoma, and displays poor specificity, with falsely elevated levels in benign conditions. Ovarian clear cell adenocarcinoma (OCCA) is the most aggressive subtype of ovarian cancer with poor prognosis and with an overall incidence of 3.7-12.1% among all histological subtypes of epithelial ovarian carcinoma (EOC) in the United States and higher incidence in Asia. OCCA tumors are malignant and are distinct from other subtypes owing to their strong association with endometriosis, the underlying molecular mechanisms in pathogenesis, and their relative resistance to chemotherapy (Schwartz et al. Cancer research. 2002; 62:4722-9; Takano et al. British journal of cancer. 2006; 94:1369-74; and Behbakht et al. Gynecologic oncology. 1998; 70:255-8; which are incorporated by reference herein in their entireties). The treatment of endometriosis, which is the leading cause of infertility and can develop into ovarian clear cell carcinoma, is itself complicated by a lack of diagnostic tools. Diagnosis of endometriosis relies upon differential diagnosis and laparoscopic examination. Improved tools for the detection of endometriosis can improve treatment of that condition as well as permit treatment of endometriosis-related conditions before they result in infertility and/or become malignant.

SUMMARY

The technology described herein is generally directed to diagnostic methods, assays, and systems, as well as methods of treatment, for endometriosis and related conditions (e.g. endometriotic cysts and ovarian cancer). As described in the Examples herein, the inventors have discovered that tissue and urinary levels of KIM-1 are elevated in patients with, e.g. endometriosis, endometriotic cyst, and mixed endometroid and clear cell ovarian cancer; indicating that KIM-1 is upregulated during both early and later stages of endometriosis-related disease. As described herein, KIM-1 is abundantly expressed at both mRNA and protein levels in OCCA cell lines and tissues, while absent in other tested subtypes of EOC and normal ovarian surface tissues and cell lines. These discoveries permit the treatment of, e.g. endometriosis-related conditions with modulators of KIM-1, including, for example, inhibitors, binding factors, or activators as described herein, as well as methods, assays, and systems relating to the diagnosis and prognosis of endometriosis-related conditions by detecting the level of expression of KIM-1 in a sample obtained from a subject.

In one aspect, described herein is a method of treating an endometriosis-related condition, the method comprising; administering a therapeutically effective amount of a KIM-1 inhibitor to a subject in need of treatment. In one aspect, described herein is a method of treating an endometriosis-related condition, the method comprising; administering a therapeutically effective amount of a KIM-1 binding reagent associated with a therapeutic agent to a subject in need of treatment. In some embodiments, the therapeutic agent can be a toxic moiety. In some embodiments, the endometriosis-related condition can be selected from the group consisting of: endometriosis; endometriotic cysts; endometrioid cancer; ovarian cancer; and clear cell cancer. In one aspect, described herein is a method of reducing angiogenesis, the method comprising; administering a KIM-1 inhibitor to a subject in need of treatment for angiogenesis-mediated disorder; wherein administering said KIM-1 inhibitor reduces angiogenesis in the subject. In some embodiments, the disease or disorder can be selected from the group consisting of: cancer; ovarian cancer; kidney cancer; endometriosis; atherosclerosis; adiposity; macular degeneration; age-related macular degeneration; arthritis; rheumatoid arthritis; Crohn's disease; diabetic retinopathy; neovascular glaucoma; and psoriasis.

In some embodiments, the KIM-1 inhibitor can specifically bind KIM-1 polypeptide. In some embodiments, the KIM-1 inhibitor can specifically bind KIM-1 ectodomain. In some embodiments, the KIM-1 inhibitor can reduce release of the KIM-1 ectodomain. In some embodiments, the KIM-1 inhibitor can bind glycosylated KIM-1 polypeptide. In some embodiments, the KIM-1 inhibitor can bind unglycosylated KIM-1 polypeptide. In some embodiments, the KIM-1 inhibitor can reduce signal transduction of KIM-1. In some embodiments, the KIM-1 inhibitor can reduce endocytosis.

In one aspect, described herein is an assay comprising: determining the expression level of KIM-1 in a test sample obtained from a subject; wherein an increase in the KIM-1 expression level relative to a reference level indicates the subject has a higher risk of having or developing endometriosis or an endometriosis-related condition. In some embodiments, the expression level of KIM-1 can be determined by measuring the level of KIM-1 RNA transcript. In some embodiments, the RNA transcript level can be measured using reverse transcription polymerase chain reaction (RT-PCR). In some embodiments, the expression level of KIM-1 can be determined by measuring the level of KIM-1 polypeptide. In some embodiments, the polypeptide level can be measured using immunochemistry. In some embodiments, the polypeptide level can be measured using a small molecule which specifically binds to KIM-1 and which is detectably labeled. In some embodiments, the sample can comprise a material selected from the group consisting of: a biofluid sample; serum; plasma; urine; saliva; yolk sac; an endometrial tissue sample; a tumor sample; a cyst; an ovarian cyst; cystic fluid; peritoneal fluid; pleural fluid; and a cervical swab.

In one aspect, described herein is an assay comprising: (a) contacting a biofluid test sample obtained from a subject with a detectable anti-KIM-1 antibody reagent; and (b) detecting the presence or intensity of a detectable signal; wherein an increase in the level of KIM-1 polypeptide, indicated by the level of the detectable signal, relative to a reference level indicates the subject has a higher risk of having or developing endometriosis or an endometriosis-related condition. In some embodiments, the antibody reagent can be detectably labeled or capable of generating a detectable signal.

In some embodiments of the foregoing aspects, the endometriosis-related condition can be selected from the group consisting of: endometriosis; endometriotic cysts; endometrioid cancer; ovarian cancer; and clear cell cancer. In some embodiments of the foregoing aspects, the KIM-1 polypeptide can comprise glycosylated KIM-1 polypeptide. In some embodiments of the foregoing aspects, the KIM-1 polypeptide can comprise unglycosylated KIM-1 polypeptide. In some embodiments of the foregoing aspects, the KIM-1 polypeptide can comprise the ectodomain of KIM-1 polypeptide. In some embodiments of the foregoing aspects, the expression level of KIM-1 can be normalized relative to the expression level of one or more reference genes or reference proteins. In some embodiments of the foregoing aspects, the reference expression level of KIM-1 can be the expression level of KIM-1 in a prior sample obtained from the subject. In some embodiments of the foregoing aspects, an increased level of KIM-1 can be a level greater than 400 pg of KIM-1 polypeptide per mg of urinary creatine. In some embodiments of the foregoing aspects, the expression level of no more than 20 other genes can be determined. In some embodiments of the foregoing aspects, the expression level of no more than 10 other genes can be determined. In some embodiments of the foregoing aspects, the subject can be a human.

In one aspect, described herein is a method of administering a treatment for endometriosis or an endometriosis-related condition to a subject, the method comprising: determining the expression level of KIM-1 polypeptide in a test sample obtained from a subject; and administering a treatment for endometriosis or endometriosis-related condition to the subject if the expression level of KIM-1 is increased relative to a reference level. In one aspect, described herein is a method of administering a treatment for endometriosis or an endometriosis-related condition to a subject, the method comprising administering a treatment for endometriosis or the endometriosis-related condition to a subject determined to have an increased expression level of KIM-1 in a test sample obtained from the subject; wherein the expression level of KIM-1 is an increased level if it is increased relative to a reference level. In one aspect, described herein is a method of identifying a subject in need of treatment for endometriosis or endometriosis-related condition, the method comprising: determining the expression level of KIM-1 in a test sample obtained from a subject; wherein the subject is identified as being in need of treatment for endometriosis if the expression level of KIM-1 is increased relative to a reference level. In one aspect, described herein is a method of identifying a subject in need of a laparoscopic examination, the method comprising: determining the expression level of KIM-1 in a test sample obtained from a subject; wherein the subject is identified as being in need of a laparoscopic examination if the expression level of KIM-1 is increased relative to a reference level.

In some embodiments, the method can further comprise a step of determining that the subject has normal kidney function. In some embodiments, the step of determining that the subject has normal kidney function comprises a kidney function urinalysis or kidney function blood test.

In one aspect, described herein is a method of determining the efficacy of a treatment for endometriosis or an endometriosis-related condition, the method comprising: (a) determining the expression level of KIM-1 in a test sample obtained from a subject before administration of the treatment; (b) determining the expression level of KIM-1 in a test sample obtained from a subject after administration of the treatment; wherein the treatment is not efficacious if the expression level determined in step (b) is increased relative to the expression level determined in step (a). In some embodiments, the endometriosis-related condition can be selected from the group consisting of: endometriosis; endometriotic cysts; endometrioid cancer; ovarian cancer; and clear cell cancer. In some embodiments, the treatment for endometriosis can be selected from the group consisting of: a hormonal treatment; progesterone; progestin; an oral contraceptive; a hormonal contraceptive; danocrine; gentrinone; a gonadotrophin releasing hormone agonist; Lupron; danazol; an aromatase inhibitor; pentoxifylline; surgical treatment; laparoscopy; cauterization; and cystectomy. In some embodiments, the sample can comprise a material selected from the group consisting of: a biofluid sample; serum; plasma; urine; saliva; yolk sac; an endometrial tissue sample; a tumor sample; a cyst; an ovarian cyst; cystic fluid; peritoneal fluid; pleural fluid; and a cervical swab. In some embodiments, the expression level of KIM-1 can be determined by measuring the level of KIM-1 RNA transcript. In some embodiments, the RNA transcript expression product level can be measured using reverse transcription polymerase chain reaction (RT-PCR). In some embodiments, the expression level of KIM-1 can be the level of KIM-1 polypeptide. In some embodiments, an increased level of KIM-1 can be a level greater than 500 pg of KIM-1 polypeptide per mg of urinary creatine. In some embodiments, the polypeptide level can be measured using a small molecule which specifically binds to KIM-1 and which is detectably labeled. In some embodiments, the polypeptide expression product level can be measured using immunochemistry. In some embodiments, the immunochemical method can comprise; (a) contacting a biofluid test sample obtained from a subject with a detectable anti-KIM-1 antibody reagent; and (b) detecting the presence or intensity of a detectable signal; wherein the expression level of KIM-1 polypeptide is indicated by the level of the detectable signal. In some embodiments, the antibody reagent can be detectably labeled or capable of generating a detectable signal. In some embodiments, the KIM-1 polypeptide can comprise glycosylated KIM-1 polypeptide. In some embodiments, the KIM-1 polypeptide can comprise unglycosylated KIM-1 polypeptide. In some embodiments, the KIM-1 polypeptide can comprise the ectodomain of KIM-1 polypeptide. In some embodiments, the endometriosis has or is at risk of progressing to a condition selected from the group consisting of: endometriotic cyst; ovarian carcinoma; and clear cell ovarian cancer. In some embodiments, the expression level of KIM-1 can be normalized relative to the expression level of one or more reference genes or reference proteins. In some embodiments, the reference expression level of KIM-1 can be the level of KIM-1 in a prior sample obtained from the subject. In some embodiments, the expression level of no more than 20 other genes can be determined. In some embodiments, the expression level of no more than 10 other genes can be determined. In some embodiments, the subject can be a human.

In one aspect, described herein is a computer system for determining the risk of a subject having or developing endometriosis or an endometriosis-related condition, the system comprising: a measuring module configured to measure the expression level of KIM-1 in a test sample obtained from a subject; a storage module configured to store output data from the determination module; a comparison module adapted to compare the data stored on the storage module with a reference level, and to provide a retrieved content, and a display module for displaying whether the sample comprises a level of KIM-lwhich is significantly increased relative to the reference expression level and/or displaying the relative expression level of KIM-1. In some embodiments, the measuring module can measure the intensity of a detectable signal from an assay indicating the expression level of KIM-1 polypeptide in the test sample. In some embodiments, the assay can be an immunoassay. In some embodiments, the measuring module can measure the intensity of a detectable signal from a RT-PCR assay indicating the expression level of KIM-1 RNA transcript in the test sample. In some embodiments, if the computing module determines that the expression level of KIM-1 in the test sample obtained from a subject is greater by a statistically significant amount than the reference expression level, the display module can display a signal indicating that the expression levels in the sample obtained from a subject are greater than those of the reference expression level. In some embodiments, the signal can indicate that the subject has an increased likelihood of having or developing endometriosis. In some embodiments, the signal can indicate the subject is in need of treatment for endometriosis. In some embodiments, the signal can indicate the degree to which the expression level of KIM-1 in the sample obtained from a subject varies from the reference expression level. In some embodiments, the endometriosis-related condition can be selected from the group consisting of: endometriosis; endometriotic cysts; endometrioid cancer; ovarian cancer; and clear cell cancer.

BRIEF DESCRIPTION OF THE DRAWINGS

FIG. 2A depicts a graph of total RNA from cell lines derived from serous (DOV13, SKOV3), mucinous (MCAS, RMUG-L, RMUG-S) and clear cell (ES2, TOV21G, RMG1) ovarian cancer, primary human ovarian surface epithelium cells (HOSE, HOSE 2) and immortalized HOSE cells (HOSE 420, HOSE 693). RNA was isolated, converted to cDNA, and KIM-1 mRNA expression was evaluated using realtime PCR; levels are normalized to internal 18S control. FIG. 2B depicts a graph of the level of KIM-1 ectodomain shed into the media the cells are grown in. The KIM-1 ectodomain shed by the different subtypes of ovarian carcinoma cells was measured using a microbead based luminex assay. KIM-1 was shed by clear cell ovarian cell lines. (*P<0.005)

FIG. 3A depicts the results of quantitative real-time PCR performed using RNA isolated from ovarian cancer cells isolated from the LCM microdissected cancerous cells from the slides of individual cancer patients and normalized to housekeeping gene expression. FIG. 3B depicts photomicrographs of immunohistochemical staining for KIM-1 in TMAs containing cores from several subtypes of epithelial ovarian cancer. KIM-1 protein expression was present in clear cell ovarian carcinoma but undetectable in other subtypes of ovarian carcinomas.

FIG. 5A depicts a graph of urinary KIM-1 levels measured using a microbead based assay with urine collected from ovarian cancer patients. The urinary levels of KIM-1 are significantly higher in the urine of clear cell ovarian cancer patients compared to urine collected from age matched healthy women, patients with benign gynecological conditions or patients with serous adenocarcinoma of ovary. FIG. 5B depicts graphs of ROC curve analysis of KIM-1 in differentiating clear cell ovarian cancer from healthy volunteers (HV) (AUC 0.97, p<0.0001), from benign gynecological diseases (AUC 0.95, p<0.0001), and from serous carcinoma (AUC 0.83, p<0.0001).

FIG. 6 depicts a graph of elevated levels of urinary KIM-1 in patients with endometriosis, endometriotic cyst and mixed endometrioid and clear cell ovarian cancer. ***p<0.001.

DETAILED DESCRIPTION

Figure 1:
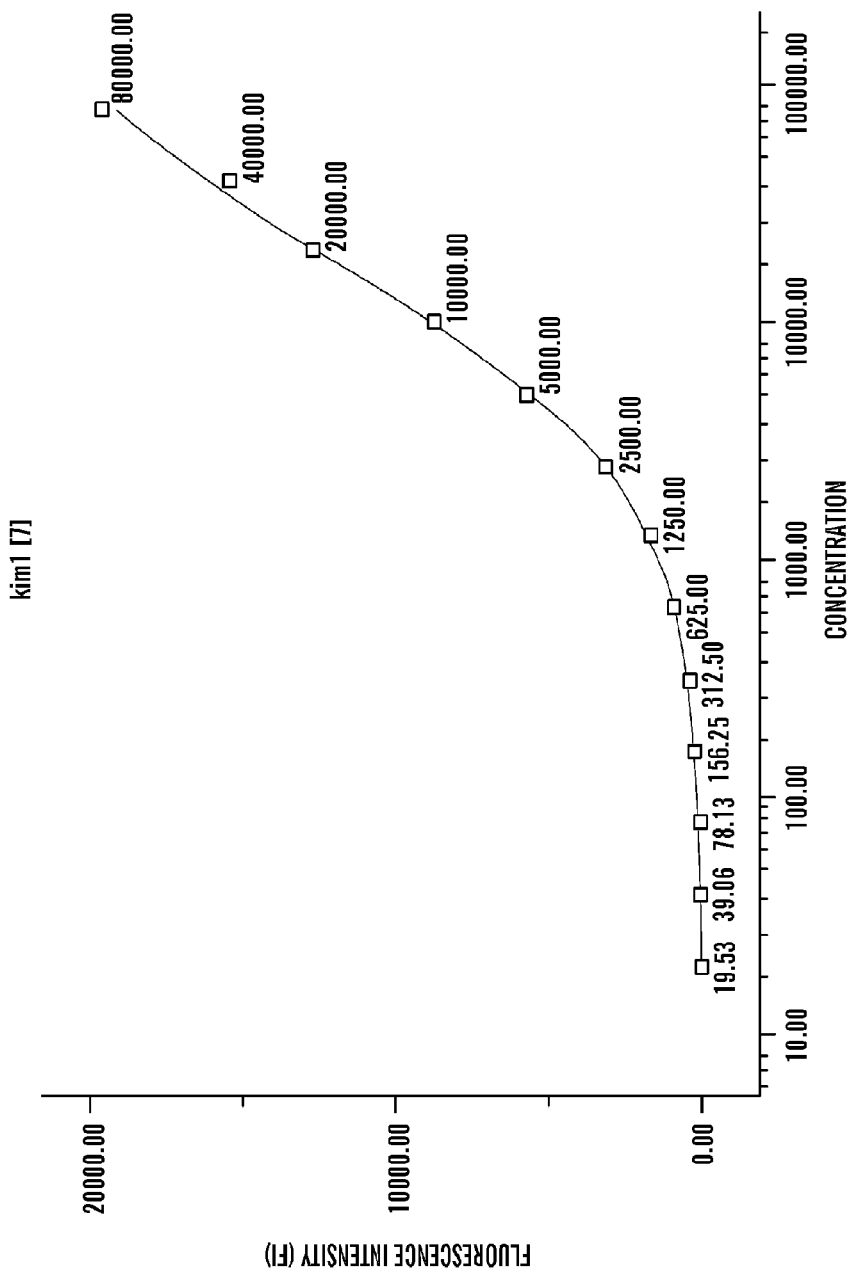
FIG. 1 depicts a graph from the evaluation of a microbead-based assay for quantitation of human urinary KIM-1: Standard curve for human KIM-1 was obtained using purified recombinant human KIM-1 ectodomain fusion protein. The assay range is 0.019-80 ng/ml.

Embodiments of the technology described herein relate to methods, assays, and systems of treating, diagnosing, and preventing, e.g. endometriosis-related conditions. The technologies described herein are based upon the inventors' discovery that subjects with endometriosis-related conditions exhibit increased levels of expression of KIM-1 (e.g. mRNA and polypeptides) as well as increased levels of cleaved KIM-1 ectodomain, which can be detected in various test samples obtained from a subject, e.g. urine or blood samples.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein generally to mean a decrease by a statistically significant amount. However, for avoidance of doubt, "reduced", "reduction", "decrease", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference level), or any decrease between 10-100% as compared to a reference level. In the context of a marker or symptom is meant a statistically significant decrease in such level. The decrease can be, for example, at least 10%, at least 20%, at least 30%, at least 40% or more, and is preferably down to a level accepted as within the range of normal for an individual without a given disorder.

The terms "increased", "increase", "enhance", or "activate" are all used herein to generally mean an increase by a statically significant amount; for the avoidance of doubt, the terms "increased", "increase", "enhance", or "activate" mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom is meant a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of, e.g. endometriosis. A subject can be male or female. In embodiments relating to endometriosis and/or ovarian cancer, a subject can be female.

A subject can be one who has been previously diagnosed with or identified as suffering from or having a condition in need of treatment (e.g. endometriosis or ovarian cancer) or one or more complications related to such a condition, and optionally, have already undergone treatment for, e.g., endometriosis or the one or more complications related to endometriosis.

Symptoms of endometriosis can include, but are not limited to, pelvic pain, infertility, and endometrial adhesions, and endometrial hemorrhagic or fibrotic foci. Alternatively, a subject can also be one who has not been previously diagnosed as having, e.g., endometriosis or one or more complications related to endometriosis. For example, a subject can be one who exhibits one or more risk factors for, e.g., endometriosis or one or more complications related to endometriosis or a subject who does not exhibit risk factors.

The inventors have found that KIM-1 stimulates angiogenesis. For example, uptake of apoptotic cells by KIM-1 results in enhanced angiopoetin-2 and VEGF production. Similarly, conditioned media from KIM-1 expressing cells that have taken up apoptotic cells cause endothelial cells to proliferate more and to generate more endothelial cell tube-like structures. Accordingly, the methods and compositions described herein can relate to the treatment of a disease or condition characterized by undesirable levels of angiogenesis. In some embodiments, a subject can be one with a disease or condition characterized by undesirable levels of angiogenesis, i.e. a condition in which the level of angiogenesis in one or more tissues of the subject is higher than in undiseased tissue of the same type. Non-limiting examples of such conditions include, but are not limited to, endometriosis and endometriosis-related conditions as described herein, and cancer.

A "subject in need" of treatment for a particular condition can be a subject having that condition, diagnosed as having that condition, or at risk of developing that condition.

As used herein, the term "antibody reagent" refers to a polypeptide that includes at least one immunoglobulin variable domain or immunoglobulin variable domain sequence and which specifically binds a given antigen (e.g. KIM-1). An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883. Antibody fragments can be obtained using any appropriate technique including conventional techniques known to those of skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

As used herein, the term "antibody" refers to immunoglobulin molecules and immunologically active portions of immunoglobulin molecules, i.e., molecules that contain an antigen binding site that immunospecifically bind an antigen. The terms also refers to antibodies comprised of two immunoglobulin heavy chains and two immunoglobulin light chains as well as a variety of forms besides antibodies; including, for example, Fv, Fab, and F(ab)'2 as well as bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). In some embodiments, antibody reagents, e.g. antibodies, monoclonal and chimeric antibodies useful in the methods as disclosed herein can be manufactured using well-known methods, e. g., as described in Howard and Kaser "Marking and Using Antibodies: A Practical Handbook" CRC Press (2006); which is incorporated by reference herein in its entirety.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity.

The term "label" refers to a composition capable of producing a detectable signal indicative of the presence of an antibody reagent (e.g. a bound antibody reagent). Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

As used herein, the terms "proteins" and "polypeptides" are used interchangeably to designate a series of amino acid residues connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "angiogenesis" refers to the development of blood vessels. In some instances, the term "angiogenesis", as used herein refers to the sprouting of new blood vessels from pre-existing blood vessels, characterized by endothelial cell proliferation and migration triggered by certain pathological conditions, such as the growth of solid tumors and metastasis.

A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastases. Cancers which migrate from their original location and seed vital organs can eventually lead to the death of the subject through the functional deterioration of the affected organs. As used herein, "ovarian cancer" refers to a cancer arising in, or involving, the ovaries. As used herein, "clear cell cancer" refers to a type of cancer in which the cytoplasm of the cancer cells appears clear when viewed under a microscope. Clear cell cancer can include, but is not limited to, uterine clear cell carcinoma and ovarian clear cell carcinoma.

The term "agent" refers generally to any entity which is normally not present or not present at the levels being administered to a cell. An agent can be selected from a group comprising: polynucleotides; polypeptides; small molecules; antibodies; or functional fragments thereof.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. endometriosis or a condition associated with undesirable (e.g. elevated) levels of angiogenesis. The term "treating" includes reducing or alleviating at least one adverse effect or symptom of a condition, disease or disorder associated with, e.g. endometriosis. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the one or more active agents in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject, e.g. parenteral, intravenous, intralesional, or intratumoral.

The term "statistically significant" or "significantly" refers to statistical significance and generally means a two standard deviation (2SD) difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

In one aspect, described herein are assays, methods, and systems relating to the inventors' discovery that when a subject has or is at risk of having an endometriosis-related condition, the diseased tissues and/or cells can express increased levels of KIM-1 as compared to healthy tissues of the same type. As further demonstrated herein, the ectodomain of KIM-1 expressed on the surface of cells is cleaved and released into the intracellular space. These KIM-1 fragments can migrate to the blood and circulate systemically and are detectable in blood as well as other biofluids, e.g. urine. As demonstrated in the Examples, KIM-1 expression and release of the ectodomain is increased in subjects and cells having endometriosis-related conditions. Thus, KIM-1, as well as fragments thereof (e.g. the ectodomain and/or the cleaved ectodomain of KIM-1), can be a diagnostic marker for endometriosis-related conditions as well as a therapeutic target.

As used herein, "endometriosis" refers to a condition characterized by the growth of endometrial cells (i.e. cells usually found in the lining of the uterus) outside of the uterine cavity, e.g. on the peritoneum. Endometriosis can occur on any tissue or organ, including, but not limited to, the peritoneum, the rectum, the ovary, and the fallopian tube. Endometriosis is generally a non-malignant condition. Non-limiting signs and symptoms of endometriosis can include pelvic pain, infertility, constipation, chronic fatigue, dysmenorrhea, dyspareunia, dysuria, leg pain, rectal pain, inflammation, and swelling. Because of the non-specific nature of the symptoms of endometriosis, laparoscopic examination is required to confirm a diagnosis. Early-stage endometriosis can appear as flat patches or flecks on the affected tissue. In some cases, endometriosis progresses to form endometriotic cysts, which can be filled with blood (e.g. "chocolate cysts"). Endometriosis can also lead to adhesions. As used herein, "endometriosis-related condition" refers to a group of conditions and/or diseases including endometriosis and conditions which are caused by and/or arise from the effects and/or progression of endometriosis (see, e.g. Sayasneh et al. Obstetrics and Gynecology 2011 2011:140310; which is incorporated by reference herein in its entirety). Examples of endometriosis-related conditions include, but are not limited to, endometriosis; endometriotic cysts; endometrioid cancer; ovarian cancer; clear cell cancer; and ovarian clear cell cancer. In some embodiments, an endometriosis-related condition can be endometriosis, endometriosis cysts, endometrioid ovarian cancer, and/or ovarian clear cell cancer. In some embodiments, an endometriosis-related condition can be endometriosis, endometriosis cysts, and/or ovarian clear cell cancer. In some embodiments, an endometriosis-related condition can be a non-cancerous condition, i.e. endometriosis and/or endometriosis cysts.

Endometrial polyps and/or endometriosis itself can lead to and/or involve fibrosis of the affected tissues. Endometrial polyps in particular are very fibrous, and uterine fibroids are a significant health concern. In some embodiments, the methods, assays, and systems described herein can relate to treating a subject with fibrosis, e.g. endometrial fibrosis and/or ovarian fibrosis. These types of fibrosis can contribute to infertility. Accordingly, the methods, assays, and systems described herein can relate to treating a subject with infertility and/or treating a subject in need of treatment to increase fertility. In some embodiments, the subject can be human. Endometrial and periglandular fibrosis is known to contribute to infertility in horses. In some embodiments, the subject can be a horse.

As described herein, the inventors have demonstrated that tissues affected by an endometriosis-related condition express and release increased levels of KIM-1. As used herein, "kidney injury molecule 1" or "KIM-1", refers to a type I cell membrane glycoprotein (also known as TIM-1 or HAVCR-1) upregulated in the kidney in response to proximal tubular kidney injury and which is expressed in two cytoplasmic domain splice variants. The sequence of KIM-1 for a number of species is well known in the art, e.g. human KIM-1 (e.g. SEQ ID NO: 1, NCBI Ref Seq: NP_036338; NCBI Gene ID: 26762). The ectodomain of KIM-1, comprising amino acids 1 to about 295 of SEQ ID NO: 1 can be cleaved from the full-length transmembrane polypeptide, generating a soluble peptide. The ectodomain is known to comprise glycosylation, both N-linked and O-linked, which can vary by cell type or in response to stimuli (for further discussion of KIM-1 structure, see, e.g. Zhang et al. JASN 2007 18:2704-14; which is incorporated by reference herein in its entirety).

Elevated levels of KIM-1, including elevated levels of cleaved KIM-1 ectodomain, are associated with endometriosis-related conditions as demonstrated herein. Accordingly, provided herein are methods of treating endometriosis-related conditions. In one aspect, described herein is a method of treating an endometriosis-related condition, the method comprising administering a therapeutically effective amount of a KIM-1 inhibitor to a subject in need of treatment.

As used herein, the term "inhibitor of KIM-1" refers to an agent that can decrease the expression level and/or activity of KIM-1, e.g. by at least 5%, at least 10%, at least 20%, at least 30%, at least 40%, at least 50%, at least 75%, at least 80%, at least 90%, at least 95%, at least 98%, at least 99% or more. In some embodiments, a KIM-1 inhibitor can decrease the level of KIM-1 mRNA, the level of KIM-1 polypeptide, the level of glycosylated KIM-1 polypeptide, the level of unglycosylated KIM-1 polypeptide, the level of soluble cleaved ectodomain present in the subject, the level of KIM-1 ectodomain released from the cell surface, and/or the level of signaling of KIM-1 in the cell of origin or a second cell. In some embodiments, a KIM-1 inhibitor can specifically bind an expression product of KIM-1. In some embodiments, a KIM-1 inhibitor can specifically bind a KIM-1 polypeptide. In some embodiments, a KIM-1 inhibitor can specifically bind the KIM-1 ectodomain, either cleaved or uncleaved. In some embodiments, a KIM-1 inhibitor can reduce release of the KIM-1 ectodomain. In some embodiments, a KIM-1 inhibitor can bind glycosylated KIM-1 polypeptide. In some embodiments, a KIM-1 inhibitor can bind unglycosylated KIM-1 polypeptide. In some embodiments, a KIM-1 inhibitor can reduce signal transduction mediated by KIM-1. In some embodiments, the KIM-1 inhibitor can reduce endocytosis (see, e.g. Kondratowicz et al. PNAS 2011 108:8426-8431 and Miyanishi et al. Nature 2007 450:435-9; which are incorporated by reference herein in their entireties).

In some embodiments, inhibitors of KIM-1 that reduce the release of the KIM-1 ectodomain can bind the juxtamembrane region of KIM-1, e.g. the ABE3 antibody described in Zhang et al. JASN 2007 18:2704-2714; which is incorporated by reference herein in its entirety. As referenced herein, the juxtamembrane region of KIM-1 is comprised by residues 242-294 of SEQ ID NO: 1. In some embodiments, inhibitors of KIM-1 that reduce the release of the KIM-1 ectodomain can bind to (or physically interact with) at least residues 272-283 of SEQ ID NO: 1. In this context, physical interaction can encompass steric hindrance of the interaction of one or more of these sites with an enzyme that cleaves the ectodomain of KIM-1. The structure of KIM-1 is further described in the art, see, e.g. Waanders et al. Journal of Pathology 2010 220:7-16; which is incorporated by reference herein in its entirety.

In some embodiments, the discovery that tissues affected by an endometriosis-related condition express increased levels of KIM-1 can be used to target therapeutic agents to the diseased cells. Accordingly, provided herein is a method of treating an endometriosis-related condition, the method comprising administering a therapeutically effective amount of a KIM-1 binding reagent associated with a therapeutic agent to a subject in need of treatment. In some embodiments, the therapeutic agent can be a toxic moiety, e.g. a chemotherapeutic agent as described elsewhere herein or any other agent which reduces survival, proliferation, and/or growth of the target cells.

It is contemplated that KIM-1 expression could be subject to regulation by, e.g. endogenous small RNAs, e.g., an miRNA or the like. To the extent that this is the case, modulation of that small RNA or its ability to interact with the regulatory machinery would also be of potential therapeutic value.

It is contemplated that in certain instances, KIM-1 may be upregulated for a beneficial purpose but that another aspect of the cancer cell may inhibit KIM-1 expression and/or activity. To the extent that this is the case, activation of KIM-1 could be of therapeutic value. Activators of KIM-1 can include, for example, agents that bind to and activate the portion of KIM-1 remaining in the original cell after cleavage.

As used herein, the term "KIM-1 binding reagent" refers to an agent that is capable of binding specifically to an expression product of KIM-1. In some embodiments, a KIM-1 binding agent can be an agent that binds specifically to a KIM-1 mRNA (e.g. an inhibitory RNA). In some embodiments, a KIM-1 binding agent can be an agent that binds specifically to a KIM-1 polypeptide (e.g. an anti-KIM-1 antibody reagent). In some embodiments, a KIM-1 binding reagent can also be an inhibitor of KIM-1.

As used herein, the term "therapeutic agent" refers to any agent that can have a therapeutic effect and/or treat an endometriosis-related condition, e.g. can decrease the severity of a sign, symptom, and/or marker of an endometriosis-related condition. The therapeutic methods described herein can be used to treat any endometriosis-related condition, including but not limited to endometriosis; endometriotic cysts; endometrioid cancer; ovarian cancer; and clear cell cancer. Examples of therapeutic agents for use in the methods described herein can include, by way of non-limiting example, aromatase inhibitors (e.g. anastrozole and letrozole). Further non-limiting examples of therapeutic agents include those that target the endocannabinoid network, e.g. selective cannabinoid receptor agonists such as WIN 55212-2, which has been reported to limit endometrial cell proliferation and control pain (see, e.g. Sanchez et al. Mol Hum Reprod 2012 18:563-571; which is incorporated by reference herein in its entirety). Further non-limiting examples of therapeutic agents include thiazolidinedione agonists of the peroxisome proliferation-activated receptor-γ (see, e.g. Leovic et al. Endocrinology 2010 151: 1846-1852; which is incorporated by reference herein in its entirety) or other anti-angiogenic strategies (see, e.g. Hum Reprod Update 2012 18:682-702; which is incorporated herein in its entirety) or progestagens.

Further non-limiting examples of therapeutic agents include anti-cancer therapeutics. Non-limiting examples of anti-cancer therapeutics can include gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN@ doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb™); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

As discussed elsewhere herein, the supernatant of KIM-1-expressing cells, especially cells exposed to apoptotic debris (as would be expected to be the case in endometriosis where there are variations in hormonal state) can contribute to angiogenesis. Accordingly, described herein is a method comprising administering a KIM-1 inhibitor to a subject in need of treatment for an angiogenesis-mediated disorder wherein administering said KIM-1 inhibitor reduces angiogenesis in the subject. A disease or disorder associated with an undesirable level of angiogenesis can be, by way of non-limiting example, cancer; ovarian cancer; kidney cancer; endometriosis; atherosclerosis; adiposity; macular degeneration; age-related macular degeneration; arthritis; rheumatoid arthritis; Crohn's disease; diabetic retinopathy; neovascular glaucoma; and psoriasis.

Due to the upregulation of KIM-1 in endometriosis and related conditions, as described herein, the level of KIM-1 can be used in methods and assays relating to the prognosis, diagnosis, and/or detection of endometriosis and endometriosis-related conditions. In some embodiments, the level of KIM-1 can be the RNA transcript level of KIM-1. In some embodiments, the level of KIM-1 can be the level of KIM-1 polypeptide.

Accordingly, described herein is an assay comprising: determining the expression level of KIM-1 in a test sample obtained from a subject; wherein an increase in the KIM-1 expression level relative to a reference level indicates the subject has a higher risk of having or developing endometriosis or an endometriosis-related condition. In some embodiments, described herein is an assay comprising contacting a biofluid test sample obtained from a subject with a detectable anti-KIM-1 antibody reagent; and detecting the presence or intensity of a detectable signal; wherein an increase in the level of KIM-1 polypeptide, indicated by the level of the detectable signal, relative to a reference level indicates the subject has a higher risk of having or developing endometriosis or an endometriosis-related condition.

In some embodiments, the expression level of KIM-1 can be measured by determining the level of an expression product of the KIM-1 gene, e.g. a KIM-1 RNA transcript or a KIM-1 polypeptide. Such molecules can be isolated, derived, or amplified from a biological sample, such as a biofluid. Assays for detecting mRNA transcripts are well known in the art and include, but are not limited to, PCR procedures, RT-PCR, Northern blot analysis, RNAse protection assay, microarray analysis, hybridization methods etc. In some embodiments, mRNA transcript expression product levels are assayed using reverse transcription polymerase chain reaction (RT-PCR).

The nucleic acid sequences of KIM-1 have been assigned NCBI accession numbers for different species such as human, mouse and rat. In particular, the NCBI accession numbers for the nucleic acid sequences of the human KIM-1 expression products are included herein (SEQ ID NOs: 2, 3, and 4). Accordingly, a skilled artisan can design appropriate primers based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; and proteinase K extraction can be used to obtain nucleic acid from blood (Roiff, A et al. PCR: Clinical Diagnostics and Research, Springer (1994)).

In general, the PCR procedure describes a method of gene amplification which is comprised of (i) sequence-specific hybridization of primers to specific genes within a nucleic acid sample or library, (ii) subsequent amplification involving multiple rounds of annealing, elongation, and denaturation using a thermostable DNA polymerase, and (iii) screening the PCR products for a band of the correct size or for hybridization to a given probe. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments, the level of KIM-1 can be the level of KIM-1 polypeptide. In some embodiments, the KIM-1 polypeptide can comprise glycosylated KIM-1 polypeptide. In some embodiments, the KIM-1 polypeptide can comprise unglycosylated KIM-1 polypeptide. In some embodiments, the KIM-1 polypeptide can comprise the ectodomain of KIM-1 polypeptide.

Detection of KIM-1 polypeptides can be according to any method known in the art. Immunological methods to detect KIM-1 polypeptides in accordance with the present technology include, but are not limited to antibody techniques such as immunohistochemistry, immunocytochemistry, flow cytometry, fluorescent-activated cell sorting (FACS), immunoblotting, radioimmunoassays, western blotting, immunoprecipitation, enzyme-linked immunosorbant assays (ELISA), and derivative techniques that make use of antibody reagents as described herein.

Immunochemical methods require the use of an antibody reagent specific for the target molecule (e.g. the antigen or in the embodiments described herein, a KIM-1 polypeptide or fragment thereof (e.g. the cleaved ectodomain of KIM-1)). In some embodiments, an antibody reagent for measuring the level of KIM-1 in a sample can be an antibody reagent specific for the ectodomain of KIM-1, (e.g. specific for a polypeptide comprising amino acids 1 to about 295 of SEQ ID NO:1 or a fragment thereof). In some embodiments, the antibody reagent can be specific for the ectodomain of KIM-1 in its native conformation.

In some embodiments, the antibody reagent can be specific for a glycolated form of the ectodomain of KIM-1, e.g. glycosylation of the domain comprising residues 1-295 of SEQ ID NO: 1. In some embodiments, the antibody reagent can be specific for the N-linked glycolated form of the ectodomain of KIM-1, e.g. the N-linked glycolated form of the domain comprising residues 1-295 of SEQ ID NO: 1. In some embodiments, the antibody reagent can be specific for the O-linked glycolated form of the ectodomain of KIM-1, e.g. the 0-linked glycolated form of the domain comprising residues 1-295 of SEQ ID NO: 1. In some embodiments, the antibody reagent can be specific for the glycolated form of the Ig domain of the ectodomain of KIM-1, e.g. the glycolated form of the domain comprising residues 1-128 of SEQ ID NO: 1. In some embodiments, the antibody reagent can be specific for the 0-linked glycolated form of the mucin domain of the ectodomain of KIM-1, e.g. the O-linked glycolated form of residues 129-272 of SEQ ID NO:1. In some embodiments, the antibody reagent can be specific for the glycolated form of the junction between the mucin domain of the ectodomain of KIM-1 and the transmembrane domain, e.g. the glycolated form of residues 272-295 of SEQ ID NO:1.

In some embodiments, the assays, methods, and/or systems described herein can comprise: an anti-KIM-1 antibody reagent, i.e. an antibody reagent specific for KIM-1 or specific for a fragment or modified version of KIM-1 (e.g.

glycosylated KIM-1). In some embodiments, the antibody reagent can be detectably labeled. In some embodiments, the antibody reagent can be attached to a solid support (e.g. bound to a solid support). In some embodiments, the solid support can comprise a particle (including, but not limited to an agarose or latex bead or particle or a magnetic particle), a bead, a nanoparticle, a polymer, a substrate, a slide, a coverslip, a plate, a dish, a well, a membrane, and/or a grating. The solid support can include many different materials including, but not limited to, polymers, plastics, resins, polysaccharides, silicon or silica based materials, carbon, metals, inorganic glasses, and membranes.

In one embodiment, an assay, method, and/or system as described herein can comprise an ELISA. In an exemplary embodiment, a first antibody reagent can be immobilized on a solid support (usually a polystyrene micro titer plate). The solid support can be contacted with a sample obtained from a subject, and the antibody reagent will bind ("capture") antigens for which it is specific (e.g. KIM-1). The solid support can then be contacted with a second labeled antibody reagent (e.g. a detection antibody reagent). The detection antibody reagent can, e.g. comprise a detectable signal, be covalently linked to an enzyme, or can itself be detected by a secondary antibody which is linked to an enzyme through bio-conjugation. The presence of a signal indicates that both the first antibody reagent immobilized on the support and the second "detection" antibody reagent have bound to an antigen, i.e. the presence of a signal indicated the presence of a KIM-1 molecule. Between each step the plate is typically washed with a mild detergent solution to remove any proteins or antibodies that are not specifically bound. After the final wash step the plate is developed by adding an enzymatic substrate to produce a visible signal, which indicates the quantity of KIM-1 polypeptides in the sample. Older ELISAs utilize chromogenic substrates, though newer assays employ fluorogenic substrates with much higher sensitivity. There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem. 22:895-904. These references are hereby incorporated by reference in their entirety.

In some embodiments, described herein is an assay to detect the amount of KIM-1 expression in a sample obtained from a subject, the assay comprising: (a) contacting a sample obtained from the subject with an anti-KIM-1 antibody reagent; (b) measuring the amount of the signal from the portion of antibody reagent bound to the sample, wherein the detection of signal from antibody reagent bound to the sample indicates the presence of KIM-1; (c) comparing the amount of signal and/or expression level with a reference level, and wherein if the expression level of KIM-1 is increased (e.g. increased by at least 2-fold compared to the reference level) the subject is identified as having, at risk of having, or being in need of treatment for an endometriosis-related condition.

In one embodiment, the assays, systems, and methods described herein can comprise a lateral flow immunoassay test (LFIA), also known as the immunochromatographic assay, or strip test to measure or determine the level of KIM-1 polypeptide in a sample. LFIAs are a simple device intended to detect the presence (or absence) of KIM-1 in a sample. There are currently many LFIA tests used for medical diagnostics either for home testing, point of care testing, or laboratory use. LFIA tests are a form of immunoassay in which the test sample flows along a solid substrate via capillary action. After the sample is applied to the test strip it encounters a colored antibody reagent which mixes with the sample, and if bound to a portion of the sample, transits the substrate encountering lines or zones which have been pretreated with a second antibody reagent. Depending upon the level of KIM-1 present in the sample the colored antibody reagent can become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water samples etc. Strip tests are also known as dip stick test, the name bearing from the literal action of "dipping" the test strip into a fluid sample to be tested. LFIA strip test are easy to use, require minimum training and can easily be included as components of point-of-care test (POCT) diagnostics to be used on site in the field. LFIA tests can be operated as either competitive or sandwich assays. Sandwich LFIAs are similar to sandwich ELISA. The sample first encounters colored particles which are labeled with antibody reagents specific for a target (e.g. a KIM-1 specific antibody reagent). The test line will also contain antibody reagents (e.g. a KIM-1 specific antibody reagent). The test line will show as a colored band in positive samples. In some embodiments, the lateral flow immunoassay can be a double antibody sandwich assay, a competitive assay, a quantitative assay or variations thereof. There are a number of variations on lateral flow technology. It is also possible to apply multiple capture zones to create a multiplex test.

A typical test strip consists of the following components: (1) sample application area comprising an absorbent pad (i.e. the matrix or material) onto which the test sample is applied; (2) conjugate or reagent pad—this contains antibody reagent(s) specific to the target which can be conjugated to colored particles (usually colloidal gold particles, or latex microspheres); (3) test results area comprising a reaction membrane—typically a hydrophobic nitrocellulose or cellulose acetate membrane onto which antibody reagents are immobilized in a line across the membrane as a capture zone or test line (a control zone may also be present, containing antibodies specific for the antibody reagents conjugated to the particles or microspheres); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line which contains an antibody that picks up free latex/gold in order to confirm the test has operated correctly.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. Nos. 10/278,676; 09/579,673 and 10/717,082, which are incorporated herein by reference in their entirety, are non-limiting examples of such lateral flow test devices. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teaching of these "dip stick" technologies as necessary for the detection of KIM-1 polypeptides.

Immunochemistry is a family of techniques based on the use of a specific antibody, wherein antibodies are used to specifically target molecules inside or on the surface of cells. In some embodiments, immunohistochemistry ("IHC") and immunocytochemistry ("ICC") techniques can be used to detect or measure the levels of KIM-1 polypeptide. IHC is the application of immunochemistry to tissue sections, whereas ICC is the application of immunochemistry to cells or tissue imprints after they have undergone specific cytological preparations such as, for example, liquid-based preparations. In some instances, signal amplification may be integrated into the particular protocol, wherein a secondary antibody, that includes a label, follows the application of an antibody reagent specific for platelets or leukocytes. Typically, for immunohistochemistry, tissue obtained from a subject and fixed by a suitable fixing agent such as alcohol, acetone, and paraformaldehyde, is sectioned and reacted with an antibody. Conventional methods for immunohistochemistry are described in Buchwalow and Bocker (Eds) "Immunohistochemistry: Basics and Methods" Springer (2010); Lin and Prichard "Handbook of Practical Immunohistochemistry" Springer (2011); which are incorporated by reference herein in their entireties. In some embodiments, immunocytochemistry may be utilized where, in general, tissue or cells obtained from a subject are fixed by a suitable fixing agent such as alcohol, acetone, and paraformaldehyde, to which is reacted an antibody. Methods of immunocytological staining of human samples is known to those of skill in the art and described, for example, in Burry "Immunocytochemistry: A Practical Guide for Biomedical Research" Springer (2009); which is incorporated by reference herein in its entirety.

In some embodiments, one or more of the antibody reagents described herein can comprise a detectable label and/or comprise the ability to generate a detectable signal (e.g. by catalyzing a reaction converting a compound to a detectable product). Detectable labels can comprise, for example, a light-absorbing dye, a fluorescent dye, or a radioactive label. Detectable labels, methods of detecting them, and methods of incorporating them into an antibody reagent are well known in the art.

In some embodiments, detectable labels can include labels that can be detected by spectroscopic, photochemical, biochemical, immunochemical, electromagnetic, radiochemical, or chemical means, such as fluorescence, chemifluoresence, or chemiluminescence; or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies), The detectable label can be linked by covalent or non-covalent means to the antibody reagent. Alternatively, a detectable label can be linked such as by directly labeling a molecule that achieves binding to the antibody reagent via a ligand-receptor binding pair arrangement or other such specific recognition molecules.

Detectable labels can include, but are not limited to radioisotopes, bioluminescent compounds, chromophores, antibodies, chemiluminescent compounds, fluorescent compounds, metal chelates, and enzymes.

In other embodiments, the detection antibody is labeled with a fluorescent compound. When the fluorescently labeled antibody is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, pefidenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfluorescein (commonly known by the abbreviations FAM and F), 6-carboxy-2',4', 7',4,7-hexachlorofluorescein (HEX), 6-carboxy-4',5'-dichloro-2',7'-dimethoxyfluroescein (JOE or N,N,N',N'-tetramethyl-6carboxyrhodamine (TAMRA, or T), 6-carboxy-X-rhodamine (ROX or R), 5-carboxyrhodamine-6G (R6G5 or G5), 6-carboxyrhodamine-60 (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes.

In some embodiments, a detectable label can be a radiolabel including, but not limited to $^{3}H$, $^{125}I$, $^{35}S$, $^{14}C$, $^{32}P$, and $^{33}P$.

In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

In some embodiments, a detectable label is a chemiluminescent label, including, but not limited to lucigenin, luminol, luciferin, isoluminol, theromatic acridinium ester, imidazole, acridinium salt and oxalate ester.

In some embodiments, a detectable label can be a spectral colorimetric label including, but not limited to colloidal gold or colored glass or plastic (e.g., polystyrene, polypropylene, and latex) beads.

In some embodiments, antibodies can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif.

An antibody reagent can also be detectably labeled using fluorescence emitting metals such as $^{152}Eu$, or others of the lanthanide series. These metals can be attached to the antibody reagent using such metal chelating groups as diethylenetriaminepentaacetic acid (DTPA) or ethylenediaminetetraacetic acid (EDTA).

In some embodiments, the KIM-1 polypeptide level can be measured using a small molecule which specifically binds to KIM-1 and which is detectably labeled.

The assays and methods as described herein can relate to determining if a subject has an increased level of KIM-1 relative to a reference level. In some embodiments, the reference level can comprise the level of KIM-1 (e.g. RNA transcript or polypeptide) in a sample of the same type taken from a subject not exhibiting any signs or symptoms of, e.g. endometriosis.

In some embodiments, an increased level of KIM-1 can be a level of KIM-1 polypeptide greater than about 400 pg of KIM-1 polypeptide per mg of uCr (urinary creatinine), wherein the uCr level is measured by Jaffe method (e.g. using a Beckman creatine analyzer) or an alternative method and the KIM-1 polypeptide is measured by ELISA assay on a dish or by a micro-bead assay as described in the methods herein (e.g. using a sandwich immunoassay using the 3F4 and 3E3 antibodies described herein) or a level equivalent thereto. Methods for measuring uCr are known in the art. In some embodiments, an increased level of KIM-1 can be a level of KIM-1 polypeptide greater than 400 pg of KIM-1 per mg of uCr, e.g. 400 pg/mg uCr or more, 500 pg/mg uCr or more, 600 pg/mg uCr or more, 600 pg/mg uCr or more, 800 pg/mg uCr or more, 1000 pg/mg uCr or more, or 2000 pg/mg uCr or more. In some embodiments, an increased level of KIM-1 can be a level of KIM-1 polypeptide greater than 513 pg of KIM-1 per mg of uCr.

In some embodiments, the reference level of KIM-1 can be the level of KIM-1 in a healthy subject not having, or not diagnosed as having, e.g., endometriosis. In some embodiments, the reference level of KIM-1 in the urine can be the level of KIM-1 in the urine of a healthy subject not having, or not diagnosed as having, e.g., endometriosis. In some embodiments, the reference level of KIM-1 in the blood can be the level of KIM-1 in the blood of a healthy subject not having, or not diagnosed as having, e.g., endometriosis. In some embodiments, the reference level can be the level in a sample of similar cell type, sample type, sample processing, and/or obtained from a subject of similar age, sex and other demographic parameters as the sample/subject for which the level of KIM-1 is to be determined. In some embodiments, the test sample and control reference sample are of the same type, that is, obtained from the same biological source, and comprising the same composition, e.g. the same number and type of cells. In some embodiments, the reference expression level of KIM-1 can be the expression level of KIM-1 in a prior sample obtained from the subject. Accordingly, in some embodiments, the level of KIM-1 which is increased can vary as demographic factors such as age, gender, genotype, environmental factors, and individual medical histories vary.

In some embodiments, a level of KIM-1 can be increased relative to a reference level if the level of KIM-1 is at least 2× the reference level, e.g. at least 2×, at least 3×, at least 4×, at least 5×, at least 6×, or greater of the reference level. In some embodiments, the expression level of KIM-1 can be normalized relative to the expression level of one or more reference genes or reference proteins. In some embodiments, the expression level of KIM-1 can be normalized relative to a reference value.

In some embodiments, the expression level of no more than 20 other genes is determined. In some embodiments, the expression level of no more than 10 other genes is determined.

The term "sample" or "test sample" as used herein denotes a sample taken or isolated from an organism, e.g., a urine sample from a subject. Exemplary biological samples include, but are not limited to, a biofluid sample; serum; plasma; urine; saliva; yolk sac; an endometrial tissue sample; a tumor sample; a cyst; an ovarian cyst; cystic fluid; peritoneal fluid; pleural fluid; and/or a cervical swab; etc. The term also includes a mixture of the above-mentioned samples. The term "test sample" also includes untreated or pretreated (or pre-processed) biological samples. In some embodiments, a test sample can comprise cells from a subject.

In some embodiments, the sample can comprise any tissue affected by symptoms or, or displaying markers of endometriosis, e.g. the sample can comprise cysts. In some embodiments, the test sample can comprise or consist of urine. In some embodiments, the test sample can comprise or consist of blood and/or blood products, e.g. serum and/or plasma. As used herein, the term "biofluid" refers to any fluid obtained from a biological source and includes, but is not limited to, blood, urine, cystic fluids, and bodily secretions.

The test sample can be obtained by removing a sample of cells from a subject, but can also be accomplished by using previously isolated cells (e.g. isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, prepared by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of KIM-1 as described herein.

In some embodiments, the methods, assays, and systems described herein can further comprise a step of obtaining a test sample from a subject. In some embodiments, the subject can be a human subject.

In some embodiments, the methods, assays, and systems described herein can comprise creating a report based on the level of KIM-1. In some embodiments, the report denotes raw values for KIM-1 in the test sample (plus, optionally, the level of KIM-1 in a reference sample) or it indicates a percentage or fold increase in KIM-1 as compared to a reference level, and/or provides a signal that the subject is at risk of having, or not having endometriosis or a related condition.

The methods, assays, and systems described herein can relate to methods of treatment, methods of determining if a subject can benefit from certain therapies, and/or methods of determining if a subject should receive a laparaoscopic examination.

In one aspect, described herein is a method of administering a treatment for endometriosis or an endometriosis-related condition to a subject, the method comprising: determining the level of KIM-1 polypeptide in a test sample obtained from a subject; and administering a treatment for endometriosis or endometriosis-related condition to the subject if the level of KIM-1 is increased relative to a reference level. In one aspect, described herein is a method of administering a treatment for endometriosis or an endometriosis-related condition to a subject, the method comprising administering a treatment for endometriosis or the endometriosis-related condition to a subject determined to have an increased level of KIM-1 in a test sample obtained from the subject; wherein the level of KIM-1 is an increased level if it is increased relative to a reference level.

Treatments for endometriosis and endometriosis-related conditions are described elsewhere herein and include, e.g. hormone therapy, surgery to remove endometriotic implants, growths, and/or cysts, and/or cancer treatments (e.g. chemotherapeutics, surgery, radiation treatment, etc). Treatments for endometriosis can include, but are not limited to, a hormonal treatment; progesterone; progestin; an oral contraceptive; a hormonal contraceptive; danocrine; gentrinone; a gonadotrophin releasing hormone agonist; Lupron; danazol; an aromatase inhibitor; pentoxifylline; surgical treatment; laparoscopy; cauterization; and cystectomy.

In one aspect, described herein is a method of identifying a subject in need of treatment for endometriosis or endometriosis-related condition, the method comprising: determining the expression level of KIM-1 in a test sample obtained from a subject; wherein the subject is identified as being in need of treatment for endometriosis if the expression level of KIM-1 is increased relative to a reference level. In one aspect, described herein is a method of identifying a subject in need of a laparoscopic examination, the method comprising: determining the expression level of KIM-1 in a test sample obtained from a subject; wherein the subject is identified as being in need of a laparoscopic examination if the expression level of KIM-1 is increased relative to a reference level.

In some embodiments, methods of treating and/or identifying subjects can further comprise a step of determining that the subject has normal kidney function. High levels of KIM-1 expression have been associated with kidney damage, and determining that the subject has normal kidney function can decrease the possibility of a false diagnosis. In some embodiments, the step of determining that the subject has normal kidney function comprises a kidney function urinalysis or kidney function blood test.

In one aspect, described herein is a method of determining the efficacy of a treatment for endometriosis or an endometriosis-related condition, the method comprising: a) determining the expression level of KIM-1 in a test sample obtained from a subject before administration of the treatment; b) determining the expression level of KIM-1 in a test sample obtained from a subject after administration of the treatment; wherein the treatment is not efficacious if the expression level determined in step (b) is increased relative to the expression level determined in step (a).

In some embodiments, the technology described herein relates to a pharmaceutical composition comprising a KIM-1 inhibitor and/or KIM-1 binding reagent as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. a KIM-1 inhibitor and/or KIM-1 binding reagent as described herein.

In some embodiments, the pharmaceutical composition comprising a KIM-1 inhibitor and/or KIM-1 binding reagent as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of a KIM-1 inhibitor and/or KIM-1 binding reagent as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a KIM-1 inhibitor and/or KIM-1 binding reagent and/or KIM-1 activating agent as disclosed herein can also be incorporated into the parenteral dosage forms of the disclosure, including conventional and controlled-release parenteral dosage forms.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the KIM-1 inhibitor and/or KIM-1 binding reagent can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, a KIM-1 binding reagent as described herein can be administered in a liposome formulation. As used herein, "lipid vesicle" or "liposome" refers to vesicles surrounded by a bilayer formed of lipid components usually including lipids optionally in combination with non-lipidic components. The interior of a vesicle is generally aqueous. One major type of liposomal composition not generally found in nature includes phospholipids other than naturally-derived phosphatidylcholine. Neutral lipid vesicle compositions, for example, can be formed from dimyristoyl phosphatidylcholine (DMPC) or dipalmitoyl phosphatidylcholine (DPPC). Anionic lipid vesicle compositions generally are formed from dimyristoyl phosphatidylglycerol. Another type of liposomal composition is formed from phosphatidylcholine (PC) such as, for example, soybean PC, and egg PC. Another type is formed from mixtures of phospholipid and/or phosphatidylcholine and/or cholesterol. Lipids for lipid vesicle or liposome formation are known in the art or described herein below. Liposomes are formed by the self-assembly of phospholipid molecules in an aqueous environment. The amphipathic phospholipid molecules form a closed bilayer sphere in an attempt to shield their hydrophilic groups from the aqueous environment, while still maintaining contact with the aqueous phase via the hydrophilic head group. The resulting closed sphere can encapsulate aqueous soluble drugs or agents such as the hemoglobin, enzyme and cofactor compositions described herein, within the bilayer membrane. Non-limiting examples of liposome compositions include those described U.S. Pat. Nos. 4,983,397; 6,476,068; 5,834,012; 5,756,069; 6,387,397; 5,534,241; 4,789,633; 4,925,661; 6,153,596; 6,057,299; 5,648,478; 6,723,338; 6,627218; U.S. Pat. App. Publication Nos: 2003/0224037; 2004/0022842; 2001/0033860; 2003/0072794; 2003/0082228; 2003/0212031; 2003/0203865; 2004/0142025; 2004/0071768; International Patent Applications WO 00/74646; WO 96/13250; WO 98/33481; Papahadjopolulos D, Allen T M, Gbizon A, et al. "Sterically stabilized liposomes. Improvements in pharmacokinetics and antitumor therapeutic efficacy" Proc Natl Acad Sci U.S.A. (1991) 88: 11460-11464; Allen T M, Martin F J. "Advantages of liposomal delivery systems for anthracyclines" Semin Oncol (2004) 31: 5-15 (suppl 13). Weissig et al. Pharm. Res. (1998) 15: 1552-1556 each of which is incorporated herein by reference in its entirety.

The methods described herein can further comprise administering a second agent and/or treatment to the subject, e.g. as part of a combinatorial therapy. Non-limiting examples of additional agents and/or therapies which can be used to treat endometriosis can include aromatase inhibitors and treatments for endometriosis and related conditions (e.g. NSAIDS, birth control, danazol, progestins, and gonadatropin-releasing hormone analogs). In embodiments relating to cancer, non-limiting examples of a second agent and/or treatment can include radiation therapy, surgery, and/or anti-cancer therapeutics as described elsewhere herein, In some embodiments, the methods described herein relate to treating a subject having or diagnosed as having an endometriosis-related condition. In some embodiments, subjects having, e.g. endometriosis can be identified by a physician using current methods of diagnosing endometriosis. By way of non-limiting example, symptoms and/or complications of endometriosis which characterize this condition and aid in diagnosis are well known in the art and include but are not limited to, pain, pelvic pain, infertility, low back pain, blood in the urine, and/or dyspareunia. Tests that may aid in a diagnosis of, e.g. endometriosis include, but are not limited to, laparoscopic examination. A family history of endometriosis can also aid in determining if a subject is likely to have endometriosis or in making a diagnosis.

The compositions and methods described herein can be administered to a subject having or diagnosed as having an endometriosis-related condition. In some embodiments, the methods described herein comprise administering an effective amount of compositions described herein, e.g. a KIM-1 binding reagent to a subject in order to alleviate a symptom of, e.g. endometriosis. As used herein, "alleviating a symptom of endometriosis" is ameliorating any condition or symptom associated with endometriosis. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, intralesional, intrauterine, injection, or intratumoral administration. Administration can be local or systemic.

The term "effective amount" as used herein refers to the amount of a therapy needed to alleviate at least one or more symptoms of the disease or disorder, and relates to a sufficient amount of pharmacological composition to provide the desired effect. The term "therapeutically effective amount" therefore refers to an amount of a therapy that is sufficient to cause a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

In some embodiments, an effective amount can be an amount which causes the extent and/or number of endometriotic growths to decrease or, at least, to increase at a lower rate than they would be expected to increase in a subject not receiving a composition as described herein. In some embodiments, an effective amount can be an amount which causes a lessening of pain as compared to the level of pain experienced by a subject prior to administration of a composition as described herein. In some embodiments, an effective amount can be an amount that decreases the amount of KIM-1 polypeptide, e.g. shed KIM-1 ectodomain present in the subject and/or KIM-1 polypeptide present in the urine of a subject by a statistically significant amount. The amount of KIM-1 polypeptide can be measured by methods known in the art and those described herein, e.g. the level of KIM-1 polypeptide in the urine of a subject can be determined by a microbead sandwich assay as described in the Examples herein. Briefly, a capture antibody (e.g. the 3F4 antibody described herein) is conjugated to beads and contacted with a sample. The beads are washed and any bound KIM-1 is detected with a detection antibody (e.g. the 3E3 antibody described herein). In some embodiments, the level of KIM-1 polypeptide in a urine sample can be normalized to the level of urinary creatinine.

In some embodiments, an effective amount of a KIM-1 inhibitor can be an amount which causes a decrease in the uptake of oxidized LDL. Oxidized LDL can be labeled with a fluorescent probe (e.g. Human DiI-labeled ox-LDL which is commercially available from Intracel; Frederick, Mass. (Cat No. RP-173)) and the uptake of fluorescent material by a cell can be quantified. Such assays are described, e.g. in Ichimura et al. J Clin Invest 2008 118:1657-1668; which is incorporated by reference herein in its entirety.

In some embodiments, an effective amount of a KIM-1 inhibitor can be an amount which causes a decrease in the uptake of apoptotic epithelial cells or lymphocytes. The apoptotic cells can be labelled, e.g. fluorescently labelled and the uptake by KIM-1-expressing cells determined in the presence and absence of a candidate KIM-1 inhibitor. Such assays are described, e.g. in Ichimura et al. J Clin Invest 2008 118:1657-1668; which is incorporated by reference herein in its entirety.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an therapeutic agent which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, an effective dose of a composition comprising a KIM-1 inhibitor and/or KIM-1 binding reagent as described herein can be administered to a patient once. In certain embodiments, an effective dose of a composition comprising a KIM-1 inhibitor and/or KIM-1 binding reagent can be administered to a patient repeatedly. For systemic administration, subjects can be administered a therapeutic amount of a composition comprising a KIM-1 inhibitor and/or KIM-1 binding and/or KIM-1 activating reagent therapy such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. A composition comprising a KIM-1 inhibitor and/or KIM-1 binding reagent can be administered over a period of time, such as over a 5 minute, 10 minute, 15 minute, 20 minute, or 25 minute period. The administration can be repeated, for example, on a regular basis, such as hourly for 3 hours, 6 hours, 12 hours or longer or such as biweekly (i.e., every two weeks) for one month, two months, three months, four months or longer.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. endometriosis by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the therapeutic. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more.

In some aspects, the invention described herein is directed to systems (and computer readable media for causing computer systems) for obtaining data from at least one sample obtained from at least one subject, the system comprising 1) a measuring module configured to measure the level of KIM-1 a test sample obtained from a subject, 2) a storage module configured to store output data from the measuring module, 3) a comparison module adapted to compare the data stored on the storage module with a reference level, and to provide a retrieved content, and 4) a display module for displaying whether the sample comprises a level of KIM-1 which is significantly increased relative to the reference expression level and/or displaying the relative expression level of KIM-1.

Figure 7:
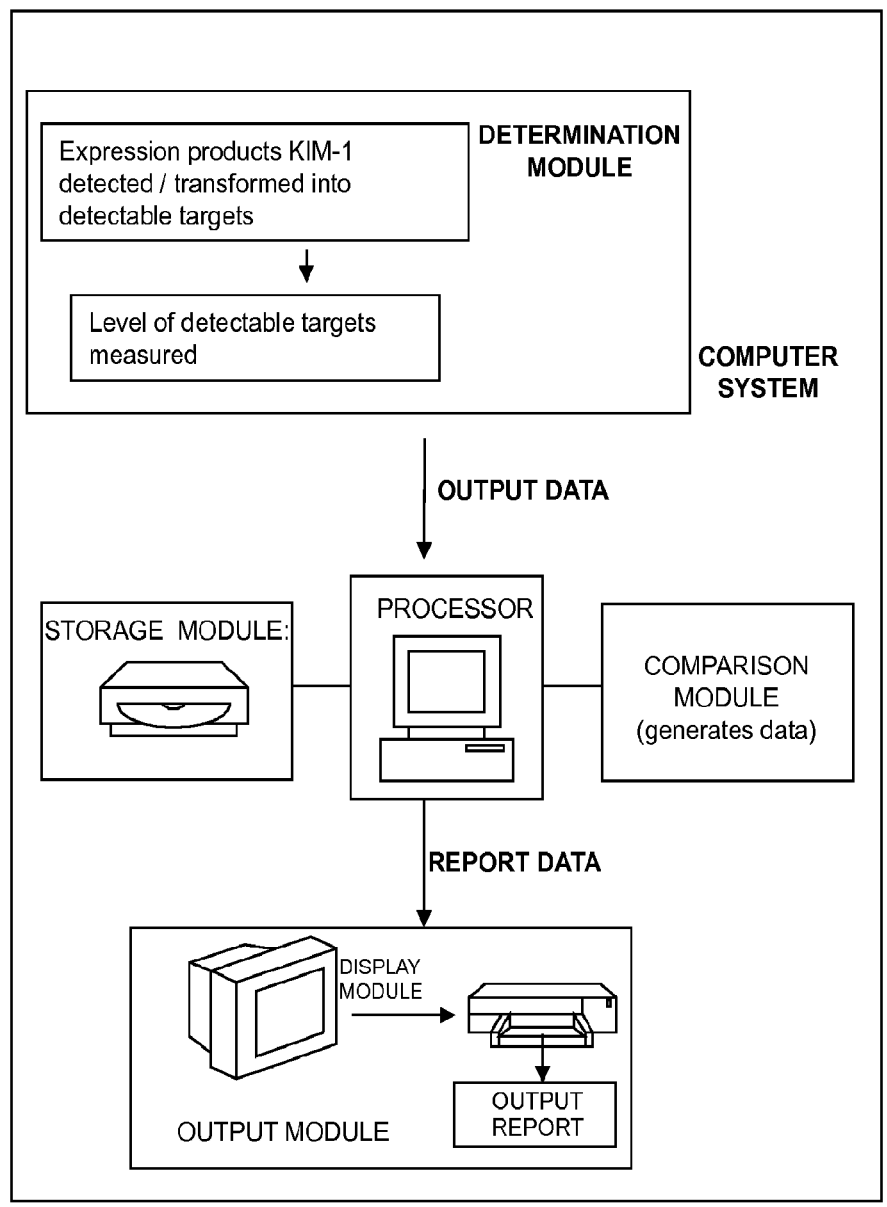
FIG. 7 is a diagram of an exemplary embodiment of a system for performing an assay for determining the level of KIM-1 in sample obtained from a subject.

In one embodiment, provided herein is a system comprising: (a) at least one memory containing at least one computer program adapted to control the operation of the computer system to implement a method that includes 1) a measuring module configured to measure the expression level of KIM-1 in a test sample obtained from a subject, 2) a storage module configured to store output data from the measuring module, 3) a computing module adapted to identify from the output data whether the level of KIM-1 in a sample obtained from a subject is statistically significantly greater than a reference level, and 4) a display module for displaying a content based in part on the data output from the measuring module, wherein the content comprises a signal indicative of the level of KIM-1 and (b) at least one processor for executing the computer program (see FIG. 7).

In some embodiments, the measuring module can measure the presence and/or intensity of a detectable signal from an assay indicating the presence and/or level of KIM-1 RNA in the test sample, e.g. from a quantitative RT-PCR assay or a next-generation sequencing assay. In some embodiments, the measuring module can measure the presence and/or intensity of a detectable signal from an immunoassay indicating the presence and/or level of KIM-1 in the test sample. Exemplary embodiments of a measuring module can include an automated immunoassay, etc.

The measuring module can comprise any system for detecting a signal elicited from an assay to determine the level of KIM-1 as described above herein. In some embodiments, such systems can include an instrument, e.g. a FACs machine (FACSARIA™) or an qRT-PCR instrument (CFX96 TOUCH™ Real-Time PCR Detection System). In another embodiment, the measuring module can comprise multiple units for different functions, such as measurement of KIM-1 polypeptide levels (and/or detectable signals from KIM-1-specific antibody reagents) and measurement of another gene or metabolite level (e.g. one or more components of a typical urinalysis for kidney function). In one embodiment, the measuring module can be configured to perform the methods described elsewhere herein, e.g. immunoassay, or detection of any detectable label or signal.

In some embodiments, the measuring system or a further module can be configured to process whole blood samples, e.g. to separate cells or portions of cells from whole blood for use in the assays described herein. In some embodiments, the measuring system or a further module can be configured to process urine samples.

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" can refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip. A transient signal or carrier wave is not a computer-readable medium as the term is used herein. The term a "computer system" may refer to a system having a computer, where the computer comprises a computer-readable medium embodying software to operate the computer. The term "software" is used interchangeably herein with "program" and refers to prescribed rules to operate a computer. Examples of software include: software; code segments; instructions; computer programs; and programmed logic.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media can define instructions, for example, as part of one or more programs that, as a result of being executed by a computer, instruct the computer to perform one or more of the functions described herein, and/or various embodiments, variations and combinations thereof. Such instructions can be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied can reside on one or more of the components of either of a system, or a computer readable storage medium described herein, can be distributed across one or more of such components.

The computer-readable media can be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions can be embodied as any type of computer code (e.g., software or microcode) that can be employed to program a computer to implement aspects of the present invention. The computer executable instructions can be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The functional modules of certain embodiments of the invention include at minimum a measuring module, a storage module, a computing module, and a display module. The functional modules can be executed on one, or multiple, computers, or by using one, or multiple, computer networks. The measuring module has computer executable instructions to provide e.g., levels of KIM-1 etc. in computer readable form.

The information determined in the measuring system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, biomolecule assayed and the level of said biomolecule. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In some embodiments of any of the systems described herein, the storage module stores the output data from the measuring module. In additional embodiments, the storage module stores reference information such as levels of KIM-1 in healthy subjects, and/or subjects not having endometriosis and/or a population of subjects not having endometriosis.

Figure 8:
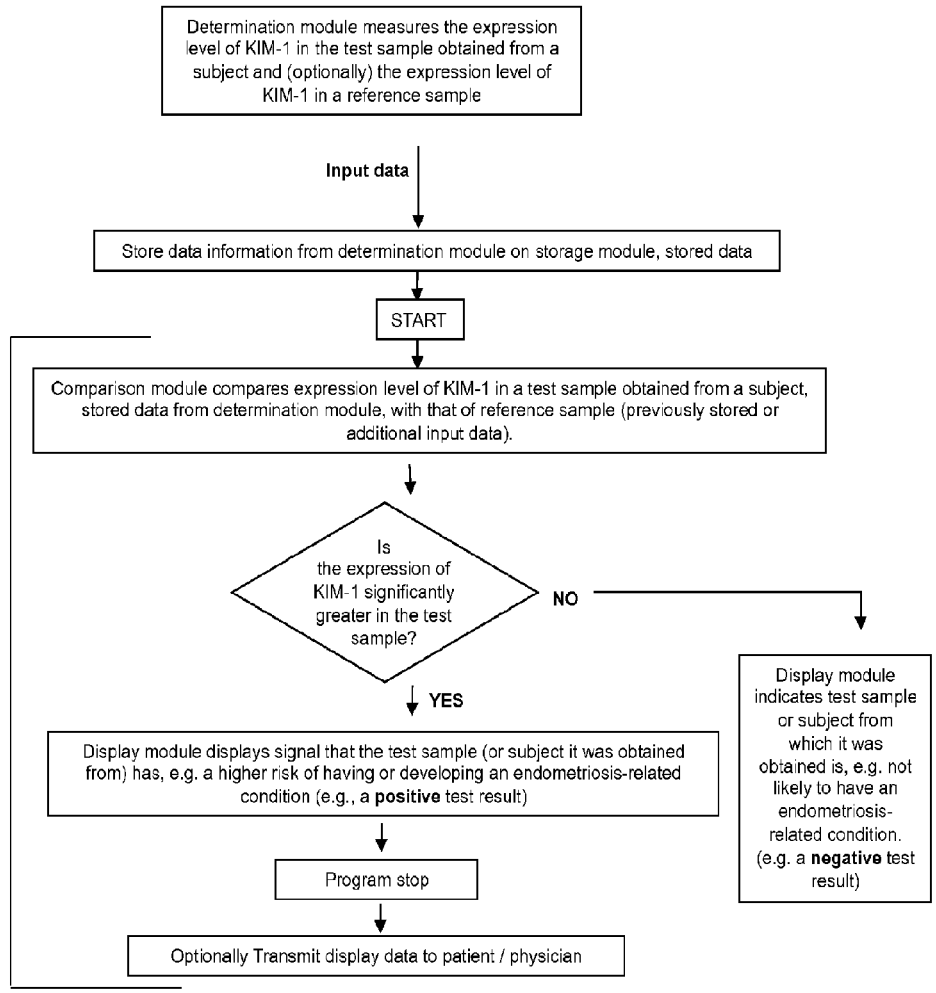
FIG. 8 is a diagram of an embodiment of a comparison module as described herein.

The "computing module" can use a variety of available software programs and formats for computing the level of platelet-adherent leukocytes. Such algorithms are well established in the art. A skilled artisan is readily able to determine the appropriate algorithms based on the size and quality of the sample and type of data. The data analysis tools and equations described herein can be implemented in the computing module of the invention. In some embodiments, the computing module can comprise a computer and/or a computer system. In one embodiment, the computing module further comprises a comparison module, which compares the level of KIM-1 in a sample obtained from a subject as described herein with a reference level as described herein (see, e.g. FIG. 8). By way of an example, when the level of KIM-1 in a sample obtained from a subject is measured, a comparison module can compare or match the output data with the mean level of KIM-1 in a population of subjects not having signs or symptoms of endometriosis (i.e. a reference level). In certain embodiments, the mean level of KIM-1 in a population of subjects not having signs or symptoms of endometriosis can be pre-stored in the storage module. During the comparison or matching process, the comparison module can determine whether the level of KIM-1 in a sample obtained from a subject is statistically significantly greater than the reference level. In various embodiments, the comparison module can be configured using existing commercially-available or freely-available software for comparison purpose, and may be optimized for particular data comparisons that are conducted.

Figure 9:
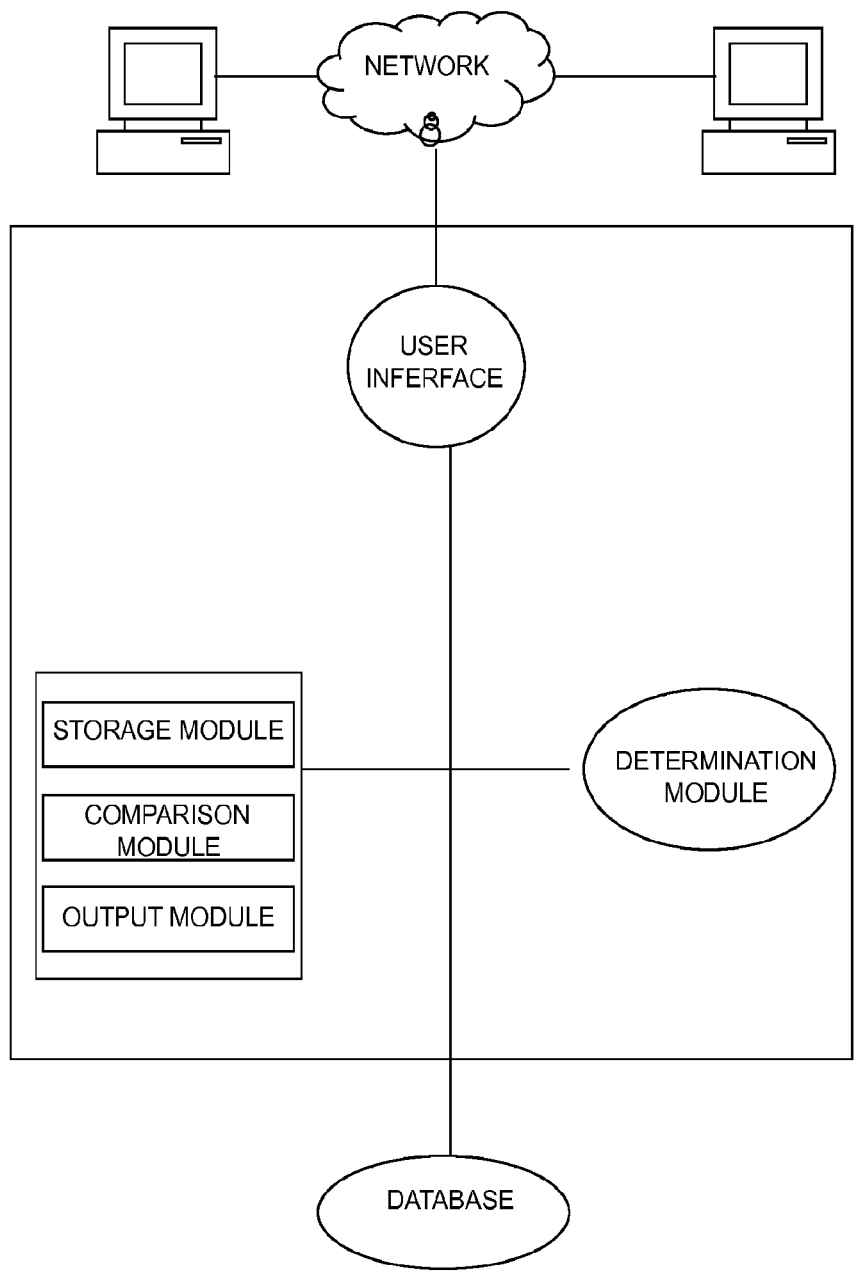
FIG. 9 is a diagram of an exemplary embodiment of an operating system and instructions for a computing system as described herein.

The computing and/or comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). In some embodiments users can directly access data (via Hypertext links for example) residing on Internet databases using a HTML interface provided by Web browsers and Web servers (see, e.g. FIG. 9).

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In some embodiments, the content displayed on the display module can be a report, e.g. the level of KIM-1 in the sample obtained from a subject. In some embodiments, a report can denote the level of KIM-1, e.g. KIM-1 RNA transcript levels and/or KIM-1 polypeptide levels. In some embodiments, a report can denote the degree to which the expression level of KIM-1 in the sample obtained from the subject varies from the reference level.

In some embodiments, if the computing module determines that the level of KIM-1 in the sample obtained from a subject is greater by a statistically significant amount than the reference level, the display module provides a report displaying a signal indicating that the level in the sample obtained from a subject is greater than that of the reference level. In some embodiments, the content displayed on the display module or report can be the relative level of KIM-1 in the sample obtained from a subject as compared to the reference level. In some embodiments, the signal can indicate the degree to which the level of KIM-1 in the sample obtained from the subject varies from the reference level. In some embodiments, the signal can indicate that the subject is at increased risk of having, e.g. endometriosis, endometriotic cysts, and/or ovarian cancer. In some embodiments, the signal can indicate the subject can benefit from treatment with a therapy for endometriosis. In some embodiments, the content displayed on the display module or report can be a numerical value indicating one of these risks or probabilities. In such embodiments, the probability can be expressed in percentages or a fraction. For example, higher percentage or a fraction closer to 1 indicates a higher likelihood of a subject having endometriosis. In some embodiments, the content displayed on the display module or report can be single word or phrases to qualitatively indicate a risk or probability. For example, a word "unlikely" can be used to indicate a lower risk for having or developing endometriosis, while "likely" can be used to indicate a high risk for having or developing endometriosis.

In one embodiment of the invention, the content based on the computing and/or comparison result is displayed on a computer monitor. In one embodiment of the invention, the content based on the computing and/or comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the computing/comparison result. It should be understood that other modules of the invention can be adapted to have a web browser interface. Through the Web browser, a user can construct requests for retrieving data from the computing/comparison module. Thus, the user will typically point and click to user interface elements such as buttons, pull down menus, scroll bars and the like conventionally employed in graphical user interfaces.

Systems and computer readable media described herein are merely illustrative embodiments of the invention for determining the level of KIM-1 in a sample obtained from a subject, and therefore are not intended to limit the scope of the invention. Variations of the systems and computer readable media described herein are possible and are intended to fall within the scope of the invention. The modules of the machine, or those used in the computer readable medium, may assume numerous configurations. For example, function may be provided on a single machine or distributed over multiple machines.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. A method of treating an endometriosis-related condition, the method comprising;
    administering a therapeutically effective amount of a KIM-1 inhibitor to a subject in need of treatment.
2. A method of treating an endometriosis-related condition, the method comprising;
    administering a therapeutically effective amount of a KIM-1 binding reagent associated with a therapeutic agent to a subject in need of treatment.
3. The method of paragraph 2, wherein the therapeutic agent is a toxic moiety.
4. The method of any of paragraphs 1-2, wherein the endometriosis-related condition is selected from the group consisting of:
    endometriosis; endometriotic cysts; endometrioid cancer; ovarian cancer; clear cell cancer; endometrial fibrosis; and ovarian fibrosis.
5. A method of reducing angiogenesis, the method comprising;
    administering a KIM-1 inhibitor to a subject in need of treatment for angiogenesis-mediated disorder;
    wherein administering said KIM-1 inhibitor reduces angiogenesis in the subject.
6. The method of paragraph 5, wherein the disease or disorder is selected from the group consisting of:
    cancer; ovarian cancer; kidney cancer; endometriosis; endometrial fibrosis; and ovarian fibrosis, atherosclerosis; adiposity; macular degeneration; age-related macular degeneration; arthritis; rheumatoid arthritis; Crohn's disease; diabetic retinopathy; neovascular glaucoma; and psoriasis.
7. The method of any of paragraphs 1-6, wherein the KIM-1 inhibitor specifically binds KIM-1 polypeptide.
8. The method of any of paragraphs 1-7, wherein the KIM-1 inhibitor specifically binds KIM-1 ectodomain.
9. The method of any of paragraphs 1-8, wherein the KIM-1 inhibitor reduces release of the KIM-1 ectodomain.
10. The method of any of paragraphs 1-9, wherein the KIM-1 inhibitor binds glycosylated KIM-1 polypeptide.
11. The method of any of paragraphs 1-9, wherein the KIM-1 inhibitor binds unglycosylated KIM-1 polypeptide.
12. The method of any of paragraphs 1-11, wherein the KIM-1 inhibitor reduces signal transduction of KIM-1.
13. The method of any of paragraphs 1-11, wherein the KIM-1 inhibitor reduces endocytosis.
14. An assay comprising:
    determining the expression level of KIM-1 in a test sample obtained from a subject;
    wherein an increase in the KIM-1 expression level relative to a reference level indicates the subject has a higher risk of having or developing endometriosis or an endometriosis-related condition.
15. The assay of paragraph 14, wherein the expression level of KIM-1 is determined by measuring the level of KIM-1 RNA transcript.
16. The assay of paragraph 15, wherein the RNA transcript level is measured using reverse transcription polymerase chain reaction (RT-PCR).
17. The assay of paragraph 14, wherein the expression level of KIM-1 is determined by measuring the level of KIM-1 polypeptide.
18. The assay of paragraph 17, wherein the polypeptide level is measured using immunochemistry.
19. The assay of paragraph 17, wherein the polypeptide level is measured using a small molecule which specifically binds to KIM-1 and which is detectably labeled.
20. The assay of any of paragraphs 14-19, wherein the sample comprises a material selected from the group consisting of:
    a biofluid sample; serum; plasma; urine; saliva; yolk sac; an endometrial tissue sample; a tumor sample; a cyst; an ovarian cyst; cystic fluid; peritoneal fluid; pleural fluid; and a cervical swab.
21. An assay comprising:
    (a) contacting a biofluid test sample obtained from a subject with a detectable anti-KIM-1 antibody reagent; and
    (b) detecting the presence or intensity of a detectable signal;
    wherein an increase in the level of KIM-1 polypeptide, indicated by the level of the detectable signal, relative to a reference level indicates the subject has a higher risk of having or developing endometriosis or an endometriosis-related condition.
22. The assay of paragraph 21, wherein the antibody reagent is detectably labeled or capable of generating a detectable signal.
23. The method of any of paragraphs 14-22, wherein the endometriosis-related condition is selected from the group consisting of:
    endometriosis; endometriotic cysts; endometrioid cancer; ovarian cancer; clear cell cancer; endometrial fibrosis; and ovarian fibrosis.
24. The assay of any of paragraphs 14-23, wherein the KIM-1 polypeptide comprises glycosylated KIM-1 polypeptide.
25. The assay of any of paragraphs 14-23, wherein the KIM-1 polypeptide comprises unglycosylated KIM-1 polypeptide.
26. The assay of any of paragraphs 14-25, wherein the KIM-1 polypeptide comprises the ectodomain of KIM-1 polypeptide.

27. The assay of any of paragraphs 14-26, wherein the expression level of KIM-1 is normalized relative to the expression level of one or more reference genes or reference proteins.

28. The assay of any of paragraphs 14-27, wherein the reference expression level of KIM-1 is the expression level of KIM-1 in a prior sample obtained from the subject.

29. The assay of any of paragraphs 14-28, wherein an increased level of KIM-1 is a level greater than 400 pg of KIM-1 polypeptide per mg of urinary creatine.

30. The assay of any of paragraphs 14-29, wherein the expression level of no more than 20 other genes is determined.

31. The assay of any of paragraphs 14-30, wherein the expression level of no more than 10 other genes is determined.

32. The assay of any of paragraphs 14-31, wherein the subject is a human.

33. A method of administering a treatment for endometriosis or an endometriosis-related condition to a subject, the method comprising:
determining the expression level of KIM-1 polypeptide in a test sample obtained from a subject; and
administering a treatment for endometriosis or endometriosis-related condition to the subject if the expression level of KIM-1 is increased relative to a reference level.

34. A method of administering a treatment for endometriosis or an endometriosis-related condition to a subject, the method comprising administering a treatment for endometriosis or the endometriosis-related condition to a subject determined to have an increased expression level of KIM-1 in a test sample obtained from the subject;
wherein the expression level of KIM-1 is an increased level if it is increased relative to a reference level.

35. A method of identifying a subject in need of treatment for endometriosis or endometriosis-related condition, the method comprising:
determining the expression level of KIM-1 in a test sample obtained from a subject;
wherein the subject is identified as being in need of treatment for endometriosis if the expression level of KIM-1 is increased relative to a reference level.

36. A method of identifying a subject in need of a laparoscopic examination, the method comprising:
determining the expression level of KIM-1 in a test sample obtained from a subject;
wherein the subject is identified as being in need of a laparoscopic examination if the expression level of KIM-1 is increased relative to a reference level.

37. The method of any of paragraphs 33-36, the method further comprising a step of determining that the subject has normal kidney function.

38. The method of paragraph 37, wherein the step of determining that the subject has normal kidney function comprises a kidney function urinalysis or kidney function blood test.

39. A method of determining the efficacy of a treatment for endometriosis or an endometriosis-related condition, the method comprising:
(a) determining the expression level of KIM-1 in a test sample obtained from a subject before administration of the treatment;
(b) determining the expression level of KIM-1 in a test sample obtained from a subject after administration of the treatment;
wherein the treatment is not efficacious if the expression level determined in step (b) is increased relative to the expression level determined in step (a).

40. The method of any of paragraphs 33-39, wherein the endometriosis-related condition is selected from the group consisting of:
endometriosis; endometriotic cysts; endometrioid cancer; ovarian cancer; and clear cell cancer; endometrial fibrosis; and ovarian fibrosis.

41. The method of any of paragraphs 33-40, wherein the treatment for endometriosis is selected from the group consisting of:
a hormonal treatment; progesterone; progestin; an oral contraceptive; a hormonal contraceptive; danocrine; gentrinone; a gonadotrophin releasing hormone agonist; Lupron; danazol; an aromatase inhibitor; pentoxifylline; surgical treatment; laparoscopy; cauterization; and cystectomy.

42. The method of any of paragraphs 33-41, wherein the sample comprises a material selected from the group consisting of:
a biofluid sample; serum; plasma; urine; saliva; yolk sac; an endometrial tissue sample; a tumor sample; a cyst; an ovarian cyst; cystic fluid; peritoneal fluid; pleural fluid; and a cervical swab.

43. The method of any of paragraphs 33-42, wherein the expression level of KIM-1 is determined by measuring the level of KIM-1 RNA transcript.

44. The method of paragraph 43, wherein the RNA transcript expression product level is measured using reverse transcription polymerase chain reaction (RT-PCR).

45. The method of any of paragraphs 33-44, wherein the expression level of KIM-1 is the level of KIM-1 polypeptide.

46. The method of any of paragraphs 33-45, wherein an increased level of KIM-1 is a level greater than 500 pg of KIM-1 polypeptide per mg of urinary creatine.

47. The assay of paragraph 45, wherein the polypeptide level is measured using a small molecule which specifically binds to KIM-1 and which is detectably labeled.

48. The method of paragraph 45, wherein the polypeptide expression product level is measured using immunochemistry.

49. The method of paragraph 47, wherein the immunochemical method comprises:
(a) contacting a biofluid test sample obtained from a subject with a detectable anti-KIM-1 antibody reagent; and
(b) detecting the presence or intensity of a detectable signal;
wherein the expression level of KIM-1 polypeptide is indicated by the level of the detectable signal.

50. The method of paragraph 49, wherein the antibody reagent is detectably labeled or capable of generating a detectable signal.

51. The method of any of paragraphs 33-50, wherein the KIM-1 polypeptide comprises glycosylated KIM-1 polypeptide.

52. The method of any of paragraphs 33-50, wherein the KIM-1 polypeptide comprises unglycosylated KIM-1 polypeptide.

53. The method of any of paragraphs 33-52, wherein the KIM-1 polypeptide comprises the ectodomain of KIM-1 polypeptide.
54. The method of any of paragraphs 33-53, wherein the endometriosis has or is at risk of progressing to a condition selected from the group consisting of: endometriotic cyst; ovarian carcinoma; and clear cell ovarian cancer.
55. The method of any of paragraphs 33-54, wherein the expression level of KIM-1 is normalized relative to the expression level of one or more reference genes or reference proteins.
56. The method of any of paragraphs 33-55, wherein the reference expression level of KIM-1 is the level of KIM-1 in a prior sample obtained from the subject.
57. The method of any of paragraphs 33-56, wherein the expression level of no more than 20 other genes is determined.
58. The method of any of paragraphs 33-57, wherein the expression level of no more than 10 other genes is determined.
59. The method of any of paragraphs 33-58, wherein the subject is a human.
60. A computer system for determining the risk of a subject having or developing endometriosis or an endometriosis-related condition, the system comprising:
    a measuring module configured to measure the expression level of KIM-1 in a test sample obtained from a subject;
    a storage module configured to store output data from the determination module;
    a comparison module adapted to compare the data stored on the storage module with a reference level, and to provide a retrieved content, and
    a display module for displaying whether the sample comprises a level of KIM-1which is significantly increased relative to the reference expression level and/or displaying the relative expression level of KIM-1.
61. The system of paragraph 60, wherein the measuring module measures the intensity of a detectable signal from an assay indicating the expression level of KIM-1 polypeptide in the test sample.
62. The system of paragraph 61, wherein assay is an immunoassay.
63. The system of paragraph 60, wherein the measuring module measures the intensity of a detectable signal from a RT-PCR assay indicating the expression level of KIM-1 RNA transcript in the test sample.
64. The system of any of paragraphs 60-63, wherein if the computing module determines that the expression level of KIM-1 in the test sample obtained from a subject is greater by a statistically significant amount than the reference expression level, the display module displays a signal indicating that the expression levels in the sample obtained from a subject are greater than those of the reference expression level.
65. The system of any of paragraphs 60-64, wherein the signal indicates that the subject has an increased likelihood of having or developing endometriosis.
66. The system of any of paragraphs 60-65, wherein the signal indicates the subject is in need of treatment for endometriosis.
67. The system of any of paragraphs 60-66, wherein the signal indicates the degree to which the expression level of KIM-1 in the sample obtained from a subject varies from the reference expression level.
68. The system of any of paragraphs 60-67, wherein the endometriosis-related condition is selected from the group consisting of:
    endometriosis; endometriotic cysts; endometrioid cancer; ovarian cancer; clear cell cancer; endometrial fibrosis; and ovarian fibrosis.

EXAMPLES

Ovarian clear cell adenocarcinoma (OCCA) is the most aggressive subtype of ovarian cancer with poor prognosis and with an overall incidence of 3.7-12.1% among all histological subtypes of epithelial ovarian carcinoma (EOC) in the United States and higher incidence in Asia. Currently, serum CA-125 is the gold standard clinical marker for the diagnosis of all subtypes of EOC. However, serum CA-125 exhibits poor sensitivity in detecting clear cell ovarian carcinoma and displays poor specificity with falsely elevated levels in benign conditions. It is described herein that Kidney Injury Molecule-1 (KIM-1) is abundantly expressed at both mRNA and protein levels in OCCA cell lines and tissues, while absent in other tested subtypes of EOC and normal ovarian surface tissues and cell lines. The results described herein demonstrate that patients with clear cell ovarian cancer have significantly higher levels of urinary KIM-1 as compared to normal, benign, and serous carcinoma with an AUC-ROC of 0.97, 0.91, & 0.83, respectively. Increased tissue and urinary KIM-1 levels were also found in patients with endometriosis, endometriotic cyst, and mixed endometroid and clear cell ovarian cancer indicating that KIM-1 may be upregulated during early stages of the disease. These findings permit diagnostic and management strategies to reduce morbidity and mortality associated with clear cell ovarian cancer.

Ovarian clear cell adenocarcinoma (OCCA) accounts for 1-12% of all epithelial ovarian cancers (EOC) in the United States and Europe (1), while the prevalence of OCCA is even higher in Asian countries, accounting for more than 15-25% of EOC (2). OCCA tumors are malignant and are distinct from other subtypes owing to their strong association with endometriosis, the underlying molecular mechanisms in pathogenesis, and their relative resistance to chemotherapy (3-5). However, the prognosis of clear cell subtype is much better than other subtypes if detected at an early stage (Stage I) (4), thereby making the identification and measurement of early biomarkers of the disease essential for prevention of clear cell ovarian cancer before it progresses to advanced stage. Epidemiological observations, histological data, and recent genomic evidence demonstrate that both endometriotic lesions and OCCA share similar somatic mutations in the AT-rich interactive domain containing protein 1A (ARID1A) (6-8) and phosphoinositide 3-kinase catalytic alpha (PI3KCA) genes illustrating a strong association between these two diseases and strongly supporting the notion that OCCA originates from putative precursor endometriotic lesions. Moreover, both clear cell ovarian carcinoma and endometriosis share similar risk factors including earlier menarche, more frequent periods with shorter cycle lengths, and lower parity (9). Thus, a marker that is upregulated at early stages of clear cell ovarian carcinoma disease could also be useful as a biomarker for endometriosis before it transforms into a malignant disease. Furthermore, such a biomarker could detect endometriosis that is not pre malignant. Endometriosis is the leading cause of infertility and is often difficult to diagnose.

Currently available screening procedures include serum CA-125 determination, bimanual pelvic examination, and transvaginal ultrasonography. Either alone or in combination, these tests lack sensitivity and specificity to be generally used for early detection (10, 11). Moreover, because of the heterogeneity of EOC, one marker alone is not sufficient for the diagnosis of all EOC subtypes (12). For instance, serum CA-125 levels are elevated in 80% of serous EOC patients with advanced disease, while only 50% of ovarian clear cell and endometrioid cancers have elevated serum CA-125 levels (12). CA-125 is present in only 50% of stage 1 cancers, when the cancer is still confined to just one ovary and has a better disease prognosis (13). Finally, as a marker of ovarian cancer, CA-125 suffers from additional shortcomings of being elevated in 2% of healthy women and elevated in the presence of benign conditions including pregnancy, uterine leiomyoma, and intra-abdominal infections (13, 14). Thus, novel, convenient, and non-invasive approaches are needed to identify clear cell ovarian cancer at an earlier stage.

The gene encoding Kidney Injury Molecule-1 (KIM-1) is located on chromosomal region 5q33.2 in humans and has been largely studied in the context of kidney injury and renal cell carcinoma (15, 16). KIM-1 is a type I transmembrane protein with an IgV domain followed by a glycosylated mucin domain and an intracellular cytoplasmic tail with multiple tyrosine phosphorylation motifs (16). KIM-1 is not detectable in normal tissues but is markedly up regulated in dedifferentiated proximal tubular epithelial cells following acute or chronic renal injury (17, 18). The ectodomain of KIM-1 (~90 kDa) is sheds from cells into the urine following proximal tubular kidney injury in both rodents and humans serving as a biomarker for renal injury (17-19). The inventors have previously demonstrated that KIM-1 is also upregulated in renal clear cell carcinoma tissues specifically in clear cell and papillary subtypes (20). When immunohistochemical analysis was used to interrogate global expression of KIM-1 in a variety of tumors using tissue microarrays, it was found that KIM-1 was upregulated only in clear cell carcinoma of the ovary and in renal cell carcinoma (21). Since KIM-1 ectodomain undergoes proteolytic cleavage, it was hypothesized that these cleaved fragments of KIM-1, in urine, can serve as a potential biomarker for diagnosis of ovarian cancer as it has for kidney injury and kidney cancer. Accordingly, as described herein, KIM-1 levels were measured in ovarian cancer cell lines, human ovarian cancer tissues, and urine specimens and its potential as a novel marker for ovarian carcinoma was evaluated. Whether KIM-1 is present in endometriosis and related pathologies and in the urine obtained from these patients with endometrial lesions was also determined.

Materials and Methods

Cell Culture. All the cell lines and cultures were maintained at 37° C. in a humidified 5% $CO_2$ incubator. Epithelial ovarian cancer cell lines derived from EOC cell lines of serous (DOV13, SKOV3), mucinous (MCAS, RMUG-L, RMUG-S) and clear cell (ES2, TOV21G, RMG1) were cultured as described previously (22). Normal human ovarian surface epithelium cells (HOSE, HOSE 2) and immortalized HOSE cells (HOSE 420, and HOSE 693) were cultured as described previously (22).

Tissue Samples. All the patient tissue specimens were collected from ovarian cancer patients who had undergone primary surgery at BWH (Boston, Mass.) under protocols approved by Institutional Review Board (IRB) at Brigham and Women's hospital Human Subject committee. Tissue specimens were cut into two parts, one part was embedded in paraffin and the other half was flash frozen in OCT embedding medium in dry ice-isopropanol bath. Histological subtype as well as clinical stage was defined by the pathologist, according to International Federation of Gynecology and Obstetrics system.

Preoperative plasma and urine samples were collected from women with ovarian cancer and benign gynecologic malignancies and from age-matched healthy controls under the institutional Review Board approval of the parent institutions. All specimens were centrifuged for 10 min at 3000 rpm to get rid of the floating particulate matter. The supernatant was collected and aliquoted in to 1.5 ml eppendorf tubes and stored at −80° C. until further analysis.

RNA Extraction and Real Time-PCR. Total RNA from cell lines was isolated using TRIZOL™ reagent according to the manufacturer's protocol and amplified using the SUPERSCRIPT™ First-Strand Synthesis System for RT-PCR (Invitrogen, Carlsbad, Calif.). Pure cancer epithelial population from cancer tissues was collected processed for RNA extraction and cDNA amplification as described previously (Aponte, 2008). RT-PCR primers for KIM-1 and 18S were purchased from IDT. Real-time PCR studies using primers for KIM-1 and 18S (housekeeping gene) were performed using Bio-Rad MYIQ™ single color Real-Time PCR detection system. All experiments were run in duplicate and repeated at least twice. KIM-1 expression was analyzed using GENE EXPRESSION MACRO™ software.

Immunohistochemistry. Immunohistochemical analysis was performed on formalin-fixed and paraffin-embedded 1 mm sections of both tissue micro array (TMA) and regular histology sections as previously described (23). Briefly, the tissue sections were de-paraffinized, dehydrated, and antigen retrieval was carried out in 0.1 M citrate buffer (pH 6.0) for 10 min. The sections were then incubated in 3% hydrogen peroxide for 5 min to ablate endogenous tissue peroxidase activity. The tissue sections were then incubated with AKG7 monoclonal antibody, at 1:8 dilution for 30 min at room temperature. The slides were stained using a DAKO ENVISION™+System horseradish peroxidase detection kit, and counterstained with hematoxylin. Clear cell RCC tissues were included as positive controls. KIM-1 positivity was evaluated by a pathologist in a blinded manner.

Monoclonal Antibody Production, Purification, and Validation. Mice were immunized with purified human KIM-1-Fc protein to generate antibodies using established antibody induction procedures by contract to A&G Precision Antibody (Columbia, Md.). Twenty-six hybridoma clones were selected that were positive for KIM-1 Fc and negative for human IgG-Fc. Hybridomas were cultured in suspension in 175-$cm^2$ tissue culture flasks in serum-free hybridoma media (BD Biosciences). The conditioned medium from these hybridomas was collected, centrifuged and monoclonal antibodies were purified using Protein-G-Sepharose column as described previously (Vaidya, 2006). The purified antibody clones were further validated using sandwich ELISA.

Generation of Biotinylated Antibodies (Detection Antibody). All the monoclonal antibodies selected in the preliminary screening were biotinylated using FLUOREPORTER BIOTIN-XX™ kit (Invitrogen) according to manufacturer's protocol. The ratio of biotin to protein (moles of biotin/mole of protein) was determined using EZ-BITOIN QUANTITATION KIT™ (Pierce). The nonreacted and hydrolyzed biotinylation reagent was removed by overnight dialysis in PBS at 4° C.

Validation of Antibodies. ELISA plates (MaxiSorp, Nuck, Naperville, Ill.) were coated with capture hKIM-1 antibodies (100 ng/ml) overnight at 4° C. in carbonate buffer. Plates were washed three times with Tween-PBS solution (PBST, 0.05% Tween-PBS) and blocked with blocking buffer (3% BSA in PBS) for 1 hr. After the incubation, plates were washed with PBST and incubated with serially diluted recombinant human KIM-1-FC (Rnd Systems) protein (0-5 ng/ml), and human acute kidney injury urine samples and control urines (positive controls) and incubated for 1.5 h at 37° C. Plates were washed with PBST, incubated in biotinylatd antibody for 1 h, followed by HRP-Streptavidin for 45 min. Color was developed by adding TMB substrate (Sigma) and the reaction was stopped within 13 min by adding 1N HCl. The absorbance was measured at 450 nm using a plate reader (Molecular Devices).

Development of KIM-1 Micro-Bead Based Assay. The antibody pair that produced good standard curve, dilution linearity, and low background was selected to further develop and evaluate the micro-bead based assay. Anti-hKIM-1 3F4 capture antibody was conjugated with COOH polystyrene beads (Bio-Rad) with amine coupling kit (Bio-Rad) using NHS-EDC chemistry according to the manufacturer's protocol. Detection antibody was developed by biotinylating Anti-hKIM-1 3E3 clone as described above. The performance characteristics of the microbead-based assay were evaluated for assay range, specificity, sensitivity, precision, recovery, linearity of dilution, and interference as described previously (19).

The concentration of KIM-1 in urine and serum samples was measured using luminex based xMAP technology developed as described above. In brief, 30 µl of urine sample was incubated in triplicate with ~6000 KIM-1 coupled beads/well for 1 hr followed by washing 3 times with PBST. The samples were then incubated with biotinylated detection antibody for 45 min followed by washing again 3 times with PBST. Quantification was achieved by incubating samples with streptavidin coupled to Picoerythrin, which is excited at 532 nm. The signal from this flourochrome was directly proportional to the amount of antigen bound at the microbead surface that was detected using the BIO-PLEX™ system (Bio-Rad). Values of unknown samples were interpolated by parametric logistic regression analysis using a 13-point standard five. All samples were analyzed in triplicate and the intra-assay variability was less than 15%.

Creatinine Measurement. Creatinine in the urine samples was measured by a Jaffe based method. Briefly, urine samples were diluted 1:10 in water and creatinine was measured using Beckman creatinine analyzer.

Statistical Analysis. All results are expressed as means±SE. Treatment means were compared with control means by ANOVA and Student's t-test. The level of significance was set at $p<0.05$ in all cases. To assess the diagnostic performance of KIM-1, receiver operating characteristic (ROC) curves were constructed and the area under the curve (AUC) and 95% confidence interval were calculated.

Results

Monoclonal Antibody Screening and KIM-1 Micro-Bead Based Assay. Mice were immunized with pure human recombinant KIM1-Fc protein. Seventeen clones producing monoclonal antibodies were selected based on their specificity to KIM-1-FC and non reactivity to IgG-Fc using a direct ELISA assay. Of the 17 clones, 3E3 and 3F4 antibody pair was selected using a sandwich ELISA method and converted the ELISA assay into a sensitive and robust micro-bead based assay format and performed extensive validation as described previously (19). The performance characteristic of the assay is described in Table 1. The sensitivity, specificity, precision profile, recovery, and linearity of the dilution of the assay were rigorously studied and were within the acceptable range (Table 1). Urinary KIM-1 values were calculated using a standard curve generated from 13 standards (0.02 ng/ml-80 ng/ml) using 5 parametric logistic regression analyses (FIG. 1).

Figure 2A:
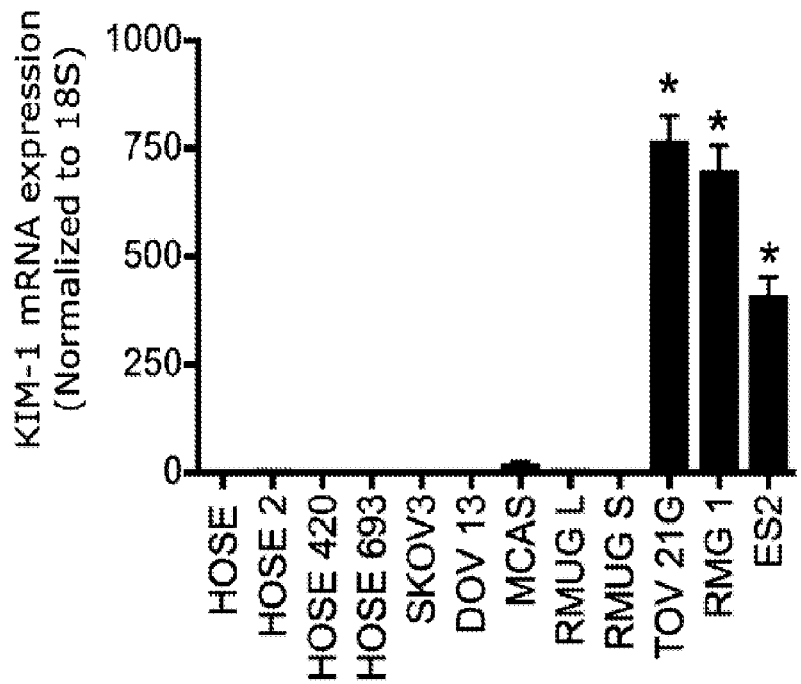
FIGS. 2A-2B demonstrate that KIM-1 is upregulated specifically in clear cell ovarian cell lines.

KIM-1 Expression is Specific to Clear Cell Subtype of Epithelial Ovarian Carcinoma. To evaluate the histotype specificity of KIM-1 expression in epithelial ovarian carcinoma subtypes, KIM-1 transcript levels were assessed in cell lines derived from serous (DOV13, SKOV3), mucinous (MCAS, RMUG-L, RMUG-S) and clear cell (ES2, TOV21G, RMG1) ovarian cancer, and compared to transcript levels in primary human ovarian surface epithelium cells (HOSE, HOSE 2) and immortalized HOSE cells (HOSE 420, and HOSE 693). As shown in FIG. 2A, KIM-1 expression was significantly higher ($P<0.005$) in clear cell lines as compared to other subtypes of EOC and normal and immortalized ovarian cell lines.

Figure 2B:
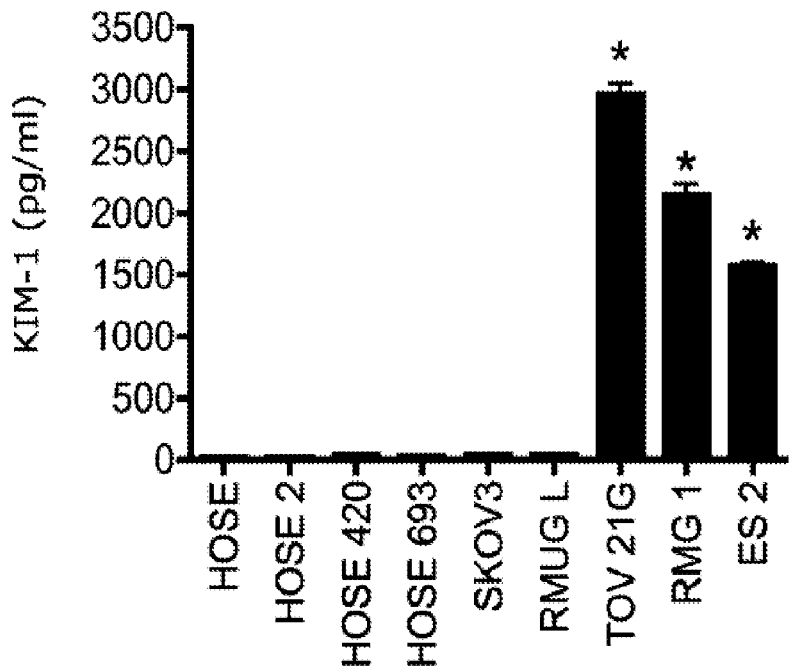

Structurally, KIM-1 possesses a cleavage sequence in its ectodomain. It was previously demonstrated that KIM-1-expressing RCC cell lines shed the 90 kDa glycosylated KIM-1 ectodomain into the supernatant (24, 25). Consistent with mRNA data, clear cell subtype cell lines secreted high levels of KIM-1 into the supernatant, while no KIM-lectodomain was detected in the supernatant collected form control HOSE and cells derived from other subtypes of epithelial ovarian cancer cell lines (FIG. 2B). Thus KIM-1 expression is limited to cells derived from the clear cell histotype.

Figure 3A:
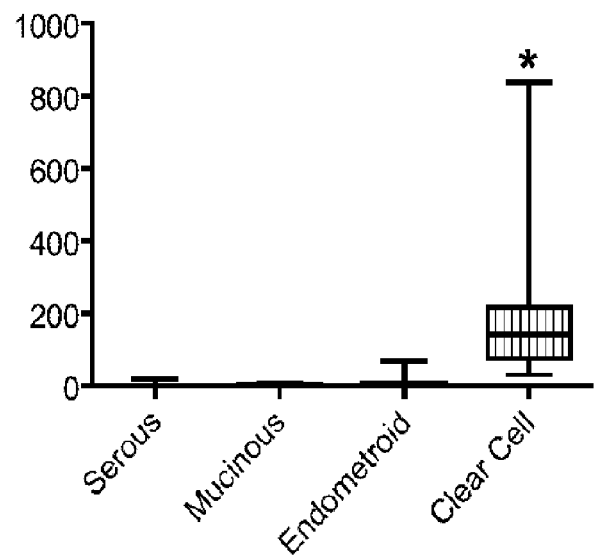
FIGS. 3A-3B demonstrate KIM-1 expression pattern in epithelial ovarian cancers.

To investigate whether these observations in vitro were consistent with findings in vivo. KIM-1 transcript levels were evaluated in enriched tumor epithelial population micro-dissected 84 epithelial ovarian cancer specimens comprising different subtypes of epithelial ovarian cancers (serous n=45, endometrioid n=12, clear cell n=13, & mucinous n=2). As shown in FIG. 3A, KIM-1 expression was significantly higher in clear cell carcinoma samples ($P<0.005$) as compared to other ovarian carcinoma subtypes. Both clear cell and endometrioid carcinomas are thought to originate from the same precursor, endometrial cells. Consistent with this common origin, some endometrioid cancers also show elevated levels of KIM-1 expression. However, the fold increase was not as high as compared to clear cell subtype.

Figure 3B:
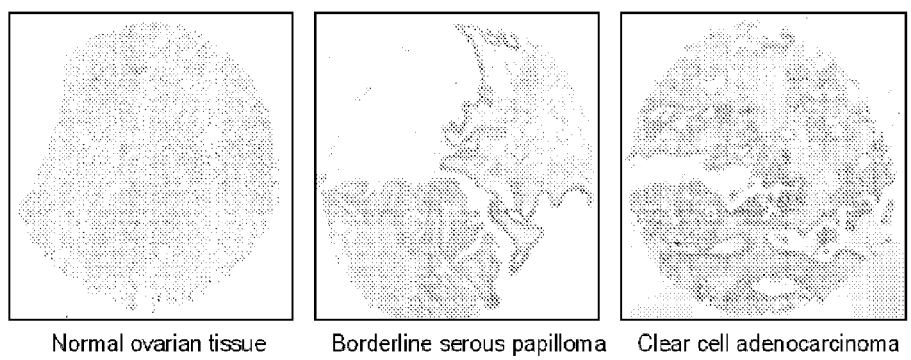
Figure 3B:
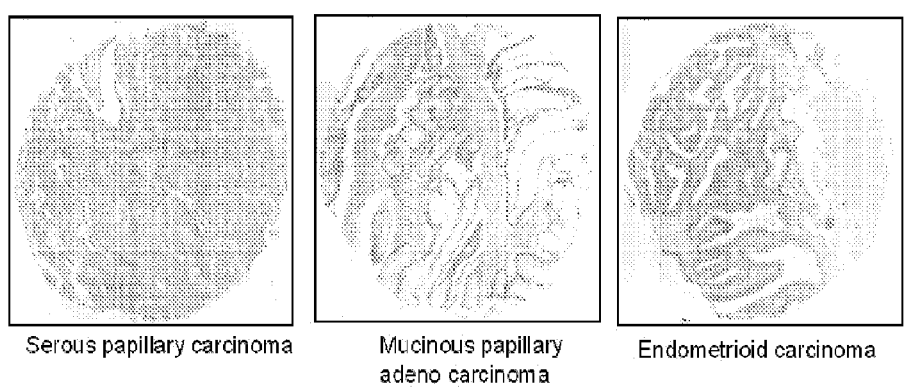

It was further confirmed KIM-1 expression patterns at the protein level in epithelial ovarian cancers using tissue microarrays constituting different histological types of tissue specimens of epithelial ovarian cancer. Consistent with findings in vitro and in vivo, KIM-1 protein expression was confined to only the clear cell histotype, while barely detectable staining was observed in other subtypes of EOC including, serous, mucinous, and endometrioid carcinoma (FIG. 3B). These data indicate that KIM-1 can be used as a marker to differentiate clear cell ovarian cancer from other epithelial ovarian cancer subtypes.

Figure 4:
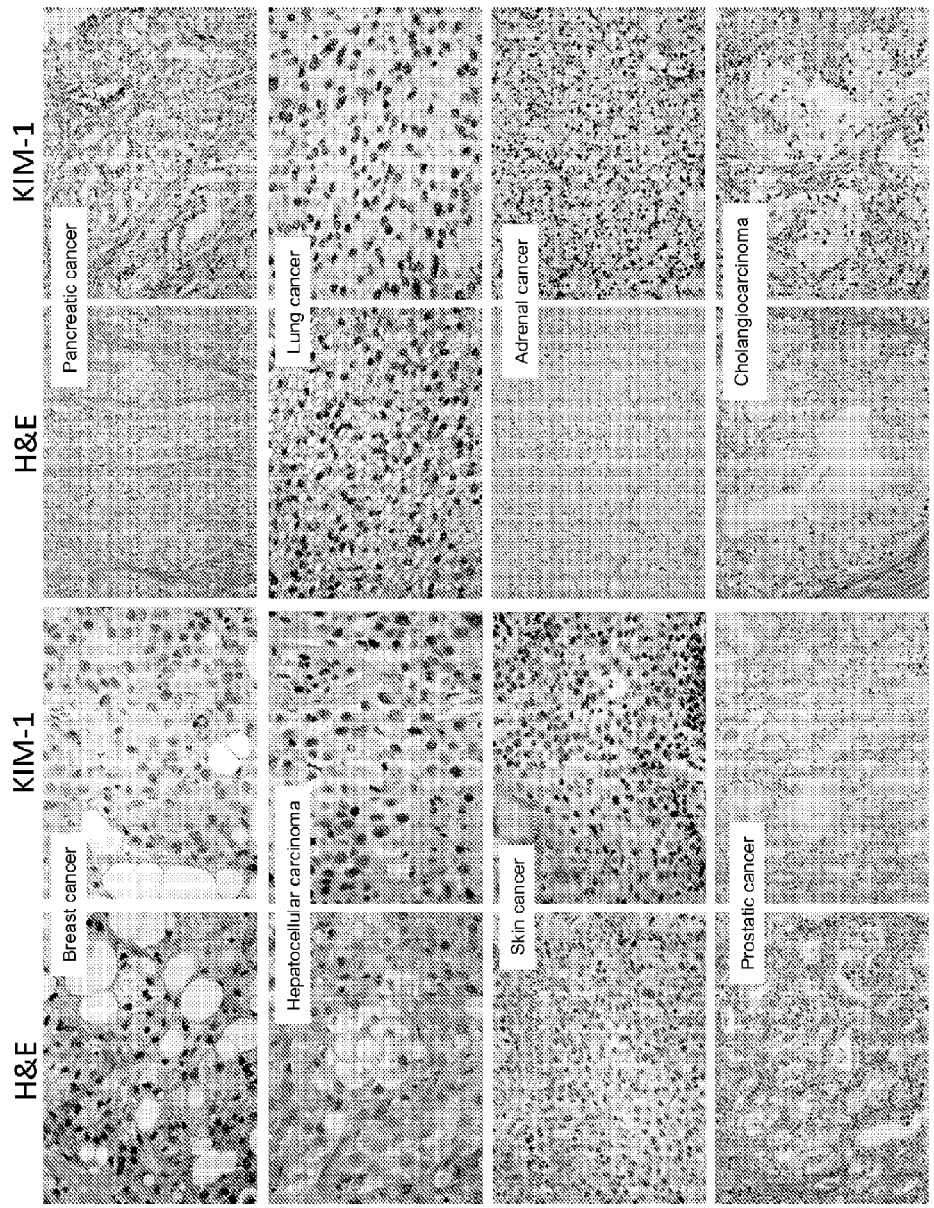
FIG. 4 depicts photomicrographs of KIM-1 expression in cancer cells. KIM-1 expression was evaluated in clear cell cancers originated from various organs including breast, liver, skin, prostate, pancreas, lung, adrenal gland, and bile duct. KIM-1 was undetectable in all these tissues.
Figure 5A:
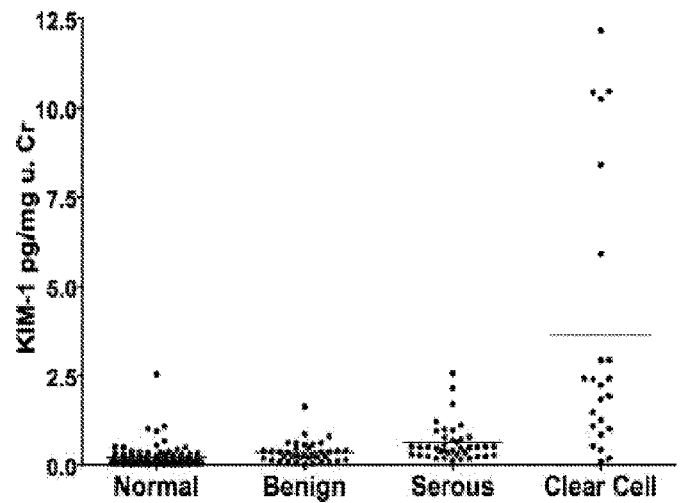
FIGS. 5A-5B demonstrate that urinary KIM-1 levels are elevated in OCCA patients.
Figure 5B:
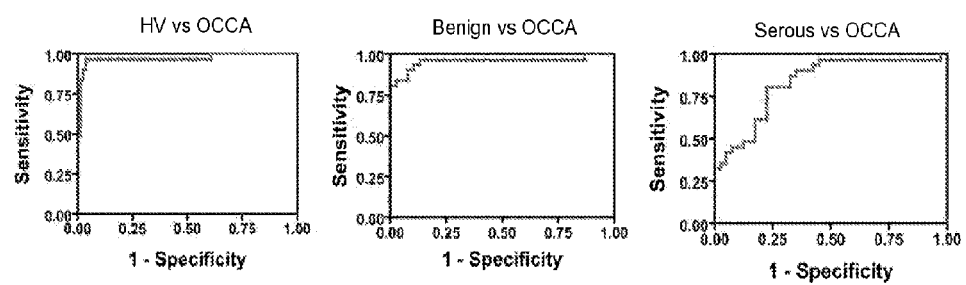

KIM-1 Expression is Organ Specific Rather than Subtype Specific. To further evaluate whether KIM-1 expression is histotype-specific or depends on the cell of origin (organ specific), KIM-1 expression was examined by immunohistochemical staining in clear cell cancers which originated from various organs including pancreatic cancer (n=6), adrenal cancer (n=6), lung cancer (n=6), breast cancer (n=6), prostate cancer (n=6), and cholangiocarcinoma (n=6). As shown in FIG. 4, KIM-1 expression is absent in all the non-ovarian and kidney clear cell carcinomas tested.

KIM-1 is a Urinary Biomarker for Clear Cell Ovarian Cancer. Since clear cell ovarian tumors express high levels of KIM-1 and cells derived from these tumors shed ectodomain into surrounding milieu, whether urinary KIM-1 levels are elevated in patients with clear cell ovarian carcinoma was determined. The KIM-1 protein was measured in urine samples collected from patients with benign gynecological diseases (n=38), serous (n=40), clear cell ovarian cancer (n=25), and from age matched healthy women (n=79). The clinical pathological parameters of these patients were outlined in Table 2. FIG. 4A shows a scatterplot of urinary KIM-1 levels in patients with and without clear cell ovarian cancer. The urinary levels of KIM-1 were significantly elevated in clear cell subtype patients (3.64±0.8 ng/mg uCr, P<0.001) as compared to age matched healthy women (0.29±0.3 ng/mg uCr, P<0.001), women with benign gynecological diseases (0.35±0.5 ng/mg uCr, P<0.001), and serous ovarian cancer (0.62±0.8 ng/mg uCr, P<0.001) patients (FIG. 4A). To eliminate the potential effects of urine output variation on biomarker levels, urinary KIM-1 levels were normalized to urine creatinine levels.

Receiver operator curve (ROC) analysis was performed to determine the performance of urinary KIM-1 in differentiating clear cell ovarian carcinoma from other EOC subtypes, healthy individuals and women with benign gynecological diseases. At a cut off value of 513 pg/mg.uCr, urinary KIM-1 had a sensitivity of 0.90 and specificity of 0.97 with an area under the curve of (AUC-ROC) of 0.971 (95% CI, 0.93-1.01) in differentiating clear cell ovarian cancer patients from healthy volunteers (FIG. 4B). The AUC-ROC of urinary KIM-1 was 0.95 (95% CI, 0.90-1.01) in distinguishing patients with benign gynecological diseases and the AUC-ROC was 0.83 (95% CI, 0.73-0.92) to differentiate a clear cell ovarian cancer patient from a serous ovarian cancer patient. Combining KIM-1 levels with serum CA125 did not significantly improve the performance of the test (data not shown). In the work described herein, 10 out of 25 clear cell ovarian cancer patients that were tested for urinary KIM-1 levels had stage I OCCA (Table 2), indicating that the increase in KIM-1 expression occurs during early stages of pathogenesis. These data indicate that urinary KIM-1 can serve as a non-invasive urinary biomarker for OCCA.

Figure 6:
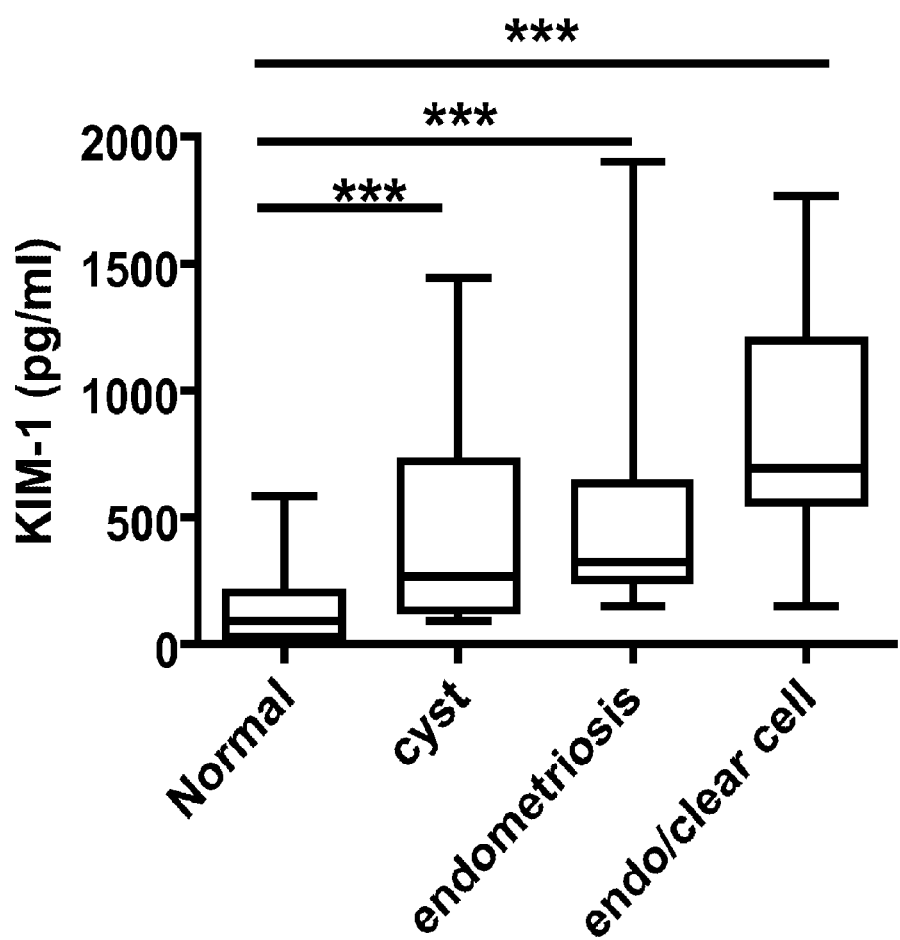
FIG. 6 demonstrates elevated levels of tissue and urinary KIM-1 in endometriosis patients.

Elevation of KIM-1 Levels in Patients with Endometriosis. Endometriosis has been identified as one of the primary risk factors for the development of clear cell ovarian cancer. The KIM-1 protein was expressed in 5 of 6 endometriosis lesions tested (data not shown). The urinary KIM-1 levels of patients with endometriosis (n=8), endometriotic cysts (n=10), and mixed endometrioid and clear cell carcinoma (n=8) were compared against age matched healthy women (n=79). As shown in FIG. 6, KIM-1 was elevated in patients with endometriosis, endometriotic cysts, and mixed endometrioid and clear cell carcinoma compared to healthy volunteers.

Discussion

In the present study, it is demonstrated that Kidney Injury Molecule-1 is specifically upregulated in clear cell subtype of ovarian cancer and its urinary levels can be used as a marker for the diagnosis of clear cell ovarian cancer. Ovarian carcinoma is a heterogeneous disease and is the most common cause of gynecologic-related mortality in women because of its asymptomatic nature and lack of early diagnostic tools (26). Clear cell carcinoma is the third most common ovarian carcinoma in North America and accounts for approximately 5% of all ovarian cancers, while it constitutes a larger percentage of ovarian cancer in the Asian population. Ovarian clear cell cancer has a distinct histopathology with poor response to chemotherapy, resulting in poor survival rate as compared to other epithelial ovarian carcinomas. However, the prognosis is much better if the disease is diagnosed at early stages.

KIM-1 is a sensitive and specific urinary marker for kidney injury and renal cell cancer. KIM-1 upregulation in renal clear cell carcinoma was expected as the tumor may be derived from proximal tubule cells that are dedifferentiated. The specific expression in clear cell ovarian carcinoma was not expected. In the current study, it is demonstrated that KIM-1 expression is markedly increased (1000 fold) in the RMG1, TOV21G, and ES2 cell lines derived from clear cell ovarian carcinoma, while completely absent in primary ovarian epithelial cells, immortalized ovarian epithelial cell lines, and ovarian cancer cell lines derived from serous and mucinous subtypes. Furthermore, KIM-1 expressing ovarian clear carcinoma cell lines shed a soluble portion of the KIM-1 ectodomain in to the medium similar to renal cell carcinoma cell lines.

The immunophenotype of clear cell ovarian carcinoma has not been extensively illustrated both because of its rare occurrence and difficulty in distinguishing this tumor with confidence from endometrioid and serum carcinomas. Because of the absence of well-studied positive markers of clear cell differentiation, pathologists mostly rely on the absence of ER and WT1 expression to distinguish clear cell from other subtypes. The results described herein clearly demonstrate that KIM-1 is specifically overexpressed in clear cell subtype and can act as a marker to distinguish OCCA from other subtypes of ovarian cancer. Notably, there was a slight elevation of KIM-1 mRNA levels in some of the endometrioid tumors that were tested. Both endometrioid and clear cell subtypes are known to be associated with endometriosis and their tissue type is close to the endometrium. The data presented herein supports the theory that both of these cancers probably share the same precursor and KIM-1 might be involved in the early steps of this pathogenesis. Further studies to explore this are warranted.

In kidney diseases, the ectodomain of KIM-1 protein is cleaved by matrix metalloproteinases and the soluble fragment (~90 kDa) is released into the lumen and excreted into the urine, serving as a biomarker. Similarly, in ovarian clear cell cancer patients, tumor tissues also shed KIM-1 ectodomain into the surrounding matrix and enter the circulation. The fully glycosylated ectodomain is approximately 90 kDa and would not be expected to get across the glomerular barrier into Bowman's space. It is possible that the protein is de-glycosylated or cleaved further in the circulation in a manner that preserves the antibody epitope. Supporting this notion, circulating levels of KIM-1 were found in patients with clear cell ovarian carcinoma (data not shown). Thus KIM-1 can be used as a urinary marker for diagnosis of clear cell carcinoma. Several studies have demonstrated that serum CA 125 levels is not a sensitive marker for clear cell ovarian carcinoma as it is elevated in only ~50% of clear cell patients and often upregulated in benign gynecological conditions. On the other hand, abundant levels of KIM-1 ectodomain are found in more than 90% of the clear cell patients that were tested. Most importantly, of the 25 clear cell carcinoma patients that were evaluated for KIM-1 levels, 10 patients had stage I indicating that KIM-1 expression occurs early in the process of carcinogenesis and hence can be used as an early diagnosis marker.

Apart from strong epidemiological and histological evidence that supports the association between endometriosis and clear cell ovarian cancer, more recent studies demonstrated that both OCCA and putative precursor endometriotic lesions share similar somatic mutations in ARID1A and PI3KCA genes, suggesting a role of endometriosis in the pathogenesis of OCCA. Early detection of endometriosis is critical for timely diagnosis and therapeutic intervention.

The mean delay in diagnosis of endometriosis is 11.7 years in US and 7.9 years in UK (27). Currently, endometriosis can be diagnosed only via laparoscopy. Thus, there is an urgent need for a sensitive and specific diagnostic test in easily accessible fluid or tissue (Plasma, Serum, Urine, etc) to detect endometriosis at early stages. The present study, demonstrates that KIM-1 levels are significantly elevated in patients with endometriosis, endometriosis with cyst, and mixed endometriosis and clear cell cancer.

The performance of urinary KIM-1 in differentiating OCCA from other subtypes of EOC was evaluated using ROC analysis. The AUC-ROC is 0.98 to distinguish a clear cell ovarian cancer patient from an age matched healthy woman. Combining urinary KIM-1 with serum CA-125 didn't increase the KIM-1 performance for detecting OCCA.

In summary, it is demonstrated herein that KIM-1 is a specific marker for clear cell carcinoma and endometriosis and can be used as a positive marker for differential diagnosis of clear cell from other subtypes. Most importantly, urinary levels of KIM-1 can be an early, non-invasive diagnostic marker for ovarian clear cell carcinoma and endometriosis.

REFERENCES

1. Goff B A, Sainz de la Cuesta R, Muntz H G, Fleischhacker D, Ek M, Rice L W, et al. Clear cell carcinoma of the ovary: a distinct histologic type with poor prognosis and resistance to platinum-based chemotherapy in stage III disease. Gynecologic oncology. 1996; 60:412-7.
2. Del Carmen M G, Birrer M, Schorge J O. Clear cell carcinoma of the ovary: A review of the literature. Gynecologic oncology. 2012.
3. Schwartz D R, Kardia S L, Shedden K A, Kuick R, Michailidis G, Taylor J M, et al. Gene expression in ovarian cancer reflects both morphology and biological behavior, distinguishing clear cell from other poor-prognosis ovarian carcinomas. Cancer research. 2002; 62:4722-9.
4. Takano M, Kikuchi Y, Yaegashi N, Kuzuya K, Ueki M, Tsuda H, et al. Clear cell carcinoma of the ovary: a retrospective multicentre experience of 254 patients with complete surgical staging. British journal of cancer. 2006; 94:1369-74.
5. Behbakht K, Randall T C, Benjamin I, Morgan M A, King S, Rubin S C. Clinical characteristics of clear cell carcinoma of the ovary. Gynecologic oncology. 1998; 70:255-8.
6. Lowery W J, Schildkraut J M, Akushevich L, Bentley R, Marks J R, Huntsman D, et al. Loss of ARID1A-associated protein expression is a frequent event in clear cell and endometrioid ovarian cancers. International journal of gynecological cancer: official journal of the International Gynecological Cancer Society. 2012; 22:9-14.
7. Wiegand K C, Shah S P, Al-Agha O M, Zhao Y, Tse K, Zeng T, et al. ARID1A mutations in endometriosis-associated ovarian carcinomas. N Engl J Med. 2010; 363: 1532-43.
8. Jones S, Wang T L, Shih Ie M, Mao T L, Nakayama K, Roden R, et al. Frequent mutations of chromatin remodeling gene ARID1A in ovarian clear cell carcinoma. Science. 2010; 330:228-31.
9. Jiang X, Morland S J, Hitchcock A, Thomas E J, Campbell I G. Allelotyping of endometriosis with adjacent ovarian carcinoma reveals evidence of a common lineage. Cancer Res. 1998; 58:1707-12.
10. Grover S, Quinn M A, Weideman P, Koh H, Robinson H P, Rome R, et al. Screening for ovarian cancer using serum CA125 and vaginal examination: report on 2550 females. Int J Gynecol Cancer. 1995; 5:291-5.
11. Markman M. Screening for ovarian cancer: is it appropriate? Journal of cancer research and clinical oncology. 1994; 120:257-8.
12. Kobel M, Kalloger S E, Boyd N, McKinney S, Mehl E, Palmer C, et al. Ovarian carcinoma subtypes are different diseases: implications for biomarker studies. PLoS medicine. 2008; 5:e232.
13. Markman M. The Role of CA-125 in the Management of Ovarian Cancer. The oncologist. 1997; 2:6-9.
14. Daoud E, Bodor G. CA-125 concentrations in malignant and nonmalignant disease. Clinical chemistry. 1991; 37:1968-74.
15. Ichimura T, Asseldonk E J, Humphreys B D, Gunaratnam L, Duffield J S, Bonventre J V. Kidney injury molecule-1 is a phosphatidylserine receptor that confers a phagocytic phenotype on epithelial cells. J Clin Invest. 2008; 118:1657-68.
16. Ichimura T, Bonventre J V, Bailly V, Wei H, Hession C A, Cate R L, et al. Kidney injury molecule-1 (KIM-1), a putative epithelial cell adhesion molecule containing a novel immunoglobulin domain, is up-regulated in renal cells after injury. J Biol Chem. 1998; 273:4135-42.
17. Ichimura T, Hung C C, Yang S A, Stevens J L, Bonventre J V. Kidney injury molecule-1: a tissue and urinary biomarker for nephrotoxicant-induced renal injury. American journal of physiology. 2004; 286:F552-63.
18. Han WbK, Bailly V, Abichandani R, Thadhani R, Bonventre JbV. Kidney Injury Molecule-1 (KIM-1): a novel biomarker for human renal proximal tubule injury. Kidney international. 2002; 62:237-44.
19. Vaidya V S, Ramirez V, Ichimura T, Bobadilla N A, Bonventre J V. Urinary kidney injury molecule-1: a sensitive quantitative biomarker for early detection of kidney tubular injury. Am J Physiol Renal Physiol. 2006; 290:F517-29.
20. Han W K, Alinani A, Wu C L, Michaelson D, Loda M, McGovern F J, et al. Human kidney injury molecule-1 is a tissue and urinary tumor marker of renal cell carcinoma. J Am Soc Nephrol. 2005; 16:1126-34.
21. Lin F, Zhang P L, Yang X J, Shi J, Blasick T, Han W K, et al. Human kidney injury molecule-1 (hKIM-1): a useful immunohistochemical marker for diagnosing renal cell carcinoma and ovarian clear cell carcinoma. The American journal of surgical pathology. 2007; 31:371-81.
22. Aponte M, Jiang W, Lakkis M, Li M J, Edwards D, Albitar L, et al. Activation of platelet-activating factor receptor and pleiotropic effects on tyrosine phospho-EGFR/Src/FAK/paxillin in ovarian cancer. Cancer Res. 2008; 68:5839-48.
23. Sabbisetti V, Di Napoli A, Seeley A, Amato A M, O'Regan E, Ghebremichael M, et al. p63 promotes cell survival through fatty acid synthase. PLoS One. 2009; 4:e5877.
24. Zhang Z, Humphreys B D, Bonventre J V. Shedding of the urinary biomarker kidney injury molecule-1 (KIM-1) is regulated by MAP kinases and juxtamembrane region. J Am Soc Nephrol. 2007; 18:2704-14.
25. Ichimura T, Bonventre J V, Bailly V, Wei H, Hession C A, Cate R L, et al. Kidney injury molecule-1 (KIM-1), a putative epithelial cell adhesion molecule containing a novel immunoglobulin domain, is up-regulated in renal cells after injury. J Biol Chem. 1998; 273:4135-42.

26. Quaye L, Gayther S A, Ramus S J, Di Cioccio R A, McGuire V, Hogdall E, et al. The effects of common genetic variants in oncogenes on ovarian cancer survival. Clin Cancer Res. 2008; 14:5833-9.
27. Hadfield R, Mardon H, Barlow D, Kennedy S. Delay in the diagnosis of endometriosis: a survey of women from the USA and the UK. Hum Reprod. 1996; 11:878-80.

TABLE 1

Performance characteristics of KIM-1 assay

| PARAMETERS | ASSAY PERFORMACE |
|---|---|
| Assay Range | 0.02-80 ng/ml |
| Lower detection limit | 7 pg/ml |
| Inter assay variability | <15% |
| Intra assay variability | <15% |
| Recovery | 85-110% |
| Linearity of dilution | 1:10, 1:20 |

TABLE 2

Clinicopathological parameters of patients.

|  | Controls (N = 79) | Benign ovarian tumors (N = 38) | Serous Ovarian Carcinoma (N = 40) | Clear cell Ovarian Carcinoma (N = 25) |
|---|---|---|---|---|
| Grade | | | | |
| Borderline | — | — | 0 | 3 |
| Invasive | — | — | 40 | 22 |
| Stage | | | | |
| I | — | — | 0 | 10 |
| II | — | — | 0 | 5 |
| III | — | — | 30 | 6 |
| IV | — | — | 10 | 2 |
| Age, median (min, max) | 57 (26, 78) | 59 (51, 65) | 58 (51, 67) | 58 (32, 72) |
| Survival status as of February 2010 | | | | |
| Alive | — | — | 14 | 19 |
| Dead | — | — | 26 | 6 |
| Median survival (months)* | — | — | 44 (1-91) | 42 (7-81) |

*using February 2010 as the censor date for those who have not died.

What is claimed herein is:

1. A method of administering a treatment for a condition selected from the group consisting of:
endometriosis; endometriotic cysts; or endometrioid cancer;
to a subject, the method comprising
administering the treatment for the condition to a subject determined to have a level of kidney injury molecule 1 (KIM-1) in a urine test sample obtained from the subject which is greater than 500 pg of KIM-1 polypeptide per mg of urinary creatinine.

2. The method of claim 1, the method further comprising a step of determining that the subject has normal kidney function.

3. The method of claim 2, wherein the step of determining that the subject has normal kidney function comprises a kidney function urinalysis or kidney function blood test.

4. The method of claim 1, wherein the treatment is selected from the group consisting of:
a hormonal treatment; progesterone; progestin; an oral contraceptive; a hormonal contraceptive; danocrine; gentrinone; a gonadotrophin releasing hormone agonist; Lupron; danazol; an aromatase inhibitor; pentoxifylline; surgical treatment; laparoscopy; cauterization; and cystectomy.

5. The method of claim 1, wherein the level of KIM-1 is determined by measuring the level of KIM-1 polypeptide.

6. The method of claim 5, wherein the KIM-1 polypeptide comprises the ectodomain of KIM-1 polypeptide.

7. The method of claim 1, wherein the endometriosis has or is at risk of progressing to a condition selected from the group consisting of:

endometriotic cyst; ovarian carcinoma; and clear cell ovarian cancer.

\* \* \* \* \*

SEQUENCE LISTING

```
<160> NUMBER OF SEQ ID NOS: 4

<210> SEQ ID NO 1
<211> LENGTH: 364
<212> TYPE: PRT
<213> ORGANISM: Homo sapiens

<400> SEQUENCE: 1

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Thr Val Pro Met Thr Thr
```

```
            145                 150                 155                 160
Val Pro Thr Thr Thr Val Pro Thr Thr Met Ser Ile Pro Thr Thr Thr
                    165                 170                 175

Thr Val Leu Thr Thr Met Thr Val Ser Thr Thr Thr Ser Val Pro Thr
                180                 185                 190

Thr Thr Ser Ile Pro Thr Thr Thr Ser Val Pro Val Thr Thr Thr Val
            195                 200                 205

Ser Thr Phe Val Pro Pro Met Pro Leu Pro Arg Gln Asn His Glu Pro
        210                 215                 220

Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                245                 250                 255

Ser Tyr Thr Thr Asp Gly Asn Asp Thr Val Thr Glu Ser Asp Ser Gly
                260                 265                 270

Leu Trp Asn Asn Asn Gln Thr Gln Leu Phe Leu Glu His Ser Leu Leu
            275                 280                 285

Thr Ala Asn Thr Thr Lys Gly Ile Tyr Ala Gly Val Cys Ile Ser Val
        290                 295                 300

Leu Val Leu Leu Ala Leu Leu Gly Val Ile Ile Ala Lys Lys Tyr Phe
305                 310                 315                 320

Phe Lys Lys Glu Val Gln Gln Leu Ser Val Ser Phe Ser Ser Leu Gln
                325                 330                 335

Ile Lys Ala Leu Gln Asn Ala Val Glu Lys Glu Val Gln Ala Glu Asp
            340                 345                 350

Asn Ile Tyr Ile Glu Asn Ser Leu Tyr Ala Thr Asp
        355                 360

<210> SEQ ID NO 2
<211> LENGTH: 1841
<212> TYPE: DNA
<213> ORGANISM: Homo sapiens

<400> SEQUENCE: 2
attctcctgc ctcagcctcc cgagtagctg ggactacagg cgccagtgac cacgcccggc    60 taatttttg tatttttagt agagacgggg tttcaccctt ttagccagga tggtctcgat   120
ctcctgactt cgtgatctgc cgccttggc ctcccaaagt gctaggatta caggtttgag   180
ccaccgcgcc cggccctgtt ccttttttgt ttgttcccct gatacctgt atcaggacca   240 ggagtcagtt tggcggttat gtgtggggaa gaagctggga agtcaggggc tgtttctgtg   300
gacagctttc cctgtccttt ggaaggcaca gagctctcag ctgcagggaa ctaacagagc   360
tctgaagccg ttatatgtgg tcttctctca tttccagcag agcaggctca tatgaatcaa   420
ccaactgggt gaaagataa gttgcaatct gagatttaag acttgatcag ataccatctg   480
gtggagggta ccaaccagcc tgtctgctca ttttccttca ggctgatccc ataatgcatc   540
ctcaagtggt catcttaagc ctcatcctac atctggcaga ttctgtagct ggttctgtaa   600
aggttggtgg agaggcaggt ccatctgtca cactaccctg ccactacagt ggagctgtca   660
catccatgtg ctggaataga ggctcatgtt ctctattcac atgccaaaat ggcattgtct   720
ggaccaatgg aacccacgtc acctatcgga aggacacacg ctataagcta ttggggacc    780 tttcaagaag ggatgtctct ttgaccatag aaaatacagc tgtgtctgac agtggcgtat   840
attgttgccg tgttgagcac cgtgggtggt tcaatgacat gaaaatcacc gtatcattgg   900
```

| | |
|---|---|
| agattgtgcc acccaaggtc acgactactc caattgtcac aactgttcca accgtcacga | 960 |
| ctgttcgaac gagcaccact gttccaacga caacgactgt tccaatgacg actgttccaa | 1020 |
| cgacaactgt tccaacaaca atgagcattc aacgacaac gactgttctg acgacaatga | 1080 |
| ctgtttcaac gacaacgagc gttccaacga caacgagcat tccaacaaca caagtgttc | 1140 |
| cagtgacaac aactgtctct acctttgttc ctccaatgcc tttgcccagg cagaaccatg | 1200 |
| aaccagtagc cacttcacca tcttcacctc agccagcaga aacccaccct acgacactgc | 1260 |
| agggagcaat aaggagagaa cccaccagct caccattgta ctcttacaca acagatggga | 1320 |
| atgacaccgt gacagagtct tcagatggcc tttggaataa caatcaaact caactgttcc | 1380 |
| tagaacatag tctactgacg gccaatacca ctaaaggaat ctatgctgga gtctgtattt | 1440 |
| ctgtcttggt gcttcttgct cttttgggtg tcatcattgc caaaaagtat ttcttcaaaa | 1500 |
| aggaggttca acaactaagt gtttcattta gcagccttca aattaaagct ttgcaaaatg | 1560 |
| cagttgaaaa ggaagtccaa gcagaagaca atatctacat tgagaatagt ctttatgcca | 1620 |
| cggactaaga cccagtggtg ctctttgaga gtttacgccc atgagtgcag aagactgaac | 1680 |
| agacatcagc acatcagacg tcttttagac cccaagacaa tttttctgtt tcagtttcat | 1740 |
| ctggcattcc aacatgtcag tgatactggg tagagtaact ctctcactcc aaactgtgta | 1800 |
| tagtcaacct catcattaat gtagtcctaa ttttttatgc t | 1841 |

<210> SEQ ID NO 3
<211> LENGTH: 1493
<212> TYPE: DNA
<213> ORGANISM: Homo sapiens

<400> SEQUENCE: 3

| | |
|---|---|
| attctcctgc ctcagcctcc cgagtagctg ggactacagg cgccagtgac cacgcccggc | 60 |
| taattttttg tatttttagt agagacgggg tttcacccct ttagccagga tggtctcgat | 120 |
| ctcctgactt cgtgatctgc ccgccttggc ctcccaaagt gctaggatta caggctgatc | 180 |
| ccataatgca tcctcaagtg gtcatcttaa gcctcatcct acatctggca gattctgtag | 240 |
| ctggttctgt aaaggttggt ggagaggcag gtccatctgt cacactaccc tgccactaca | 300 |
| gtggagctgt cacatccatg tgctggaata gaggctcatg ttctctattc acatgccaaa | 360 |
| atggcattgt ctggaccaat ggaacccacg tcacctatcg gaaggacaca cgctataagc | 420 |
| tattggggga ccttttcaaga agggatgtct ctttgaccat agaaaataca gctgtgtctg | 480 |
| acagtggcgt atattgttgc cgtgttgagc accgtgggtg gttcaatgac atgaaaatca | 540 |
| ccgtatcatt ggagattgtg ccacccaagg tcacgactac tccaattgtc acaactgttc | 600 |
| caaccgtcac gactgttcga acgagcacca ctgttccaac gacaacgact gttccaatga | 660 |
| cgactgttcc aacgacaact gttccaacaa caatgagcat tccaacgaca acgactgttc | 720 |
| tgacgacaat gactgtttca cgacaacga gcgttccaac gacaacgagc attccaacaa | 780 |
| caacaagtgt tccagtgaca caactgtctc tacctttgt tcctccaatg cctttgccca | 840 |
| ggcagaacca tgaaccagta gccacttcac catcttcacc tcagccagca gaaacccacc | 900 |
| ctacgacact gcagggagca ataaggagag aacccaccag ctcaccattg tactcttaca | 960 |
| caacagatgg gaatgacacc gtgacagagt cttcagatgg cctttggaat aacaatcaaa | 1020 |
| ctcaactgtt cctagaacat agtctactga cggccaatac cactaaagga atctatgctg | 1080 |
| gagtctgtat ttctgtcttg gtgcttcttg ctcttttggg tgtcatcatt gccaaaaagt | 1140 |
| atttcttcaa aaaggaggtt caacaactaa gtgtttcatt tagcagcctt caaattaaag | 1200 |

```
ctttgcaaaa tgcagttgaa aaggaagtcc aagcagaaga caatatctac attgagaata    1260
gtctttatgc cacggactaa gacccagtgg tgctctttga gagtttacgc ccatgagtgc    1320
agaagactga acagacatca gcacatcaga cgtcttttag accccaagac aattttttctg   1380 tttcagtttc atctggcatt ccaacatgtc agtgatactg ggtagagtaa ctctctcact    1440
ccaaactgtg tatagtcaac ctcatcatta atgtagtcct aattttttat gct           1493

<210> SEQ ID NO 4
<211> LENGTH: 1359
<212> TYPE: DNA
<213> ORGANISM: Homo sapiens

<400> SEQUENCE: 4
gttacccagc attgtgagtg acagagcctg gatctgaacg ctgatcccat aatgcatcct    60
caagtggtca tcttaagcct catcctacat ctggcagatt ctgtagctgg ttctgtaaag    120
gttggtggag aggcaggtcc atctgtcaca ctaccctgcc actacagtgg agctgtcaca    180
tccatgtgct ggaatagagg ctcatgttct ctattcacat gccaaaatgg cattgtctgg    240
accaatggaa cccacgtcac ctatcggaag gacacacgct ataagctatt gggggacctt    300
tcaagaaggg atgtctcttt gaccatagaa atacagctg tgtctgacag tggcgtatat     360
tgttgccgtg ttgagcaccg tgggtggttc aatgacatga aaatcaccgt atcattggag    420
attgtgccac ccaaggtcac gactactcca attgtcacaa ctgttccaac cgtcacgact    480
gttcgaacga gcaccactgt tccaacgaca acgactgttc caatgacgac tgttccaacg    540
acaactgttc caacaacaat gagcattcca acgacaacga ctgttctgac gacaatgact    600
gtttcaacga caacgagcgt tccaacgaca acgagcattc caacaacaac aagtgttcca    660
gtgacaacaa ctgtctctac ctttgttcct ccaatgcctt gcccaggca gaaccatgaa     720 ccagtagcca cttcaccatc ttcacctcag ccagcagaaa cccaccctac gacactgcag    780
ggagcaataa ggagagaacc caccagctca ccattgtact cttacacaac agatgggaat    840
gacaccgtga cagagtcttc agatggcctt tggaataaca atcaaactca actgttccta    900
gaacatagtc tactgacggc caataccact aaaggaatct atgctggagt ctgtatttct    960
gtcttggtgc ttcttgctct tttgggtgtc atcattgcca aaaagtattt cttcaaaaag    1020
gaggttcaac aactaagtgt ttcatttagc agccttcaaa ttaaagcttt gcaaaatgca    1080
gttgaaaagg aagtccaagc agaagacaat atctacattg agaatagtct ttatgccacg    1140
gactaagacc cagtggtgct ctttgagagt ttacgcccat gagtgcagaa gactgaacag    1200
acatcagcac atcagacgtc ttttagaccc aagacaatt tttctgtttc agtttcatct    1260
ggcattccaa catgtcagtg atactgggta gagtaactct ctcactccaa actgtgtata   1320
gtcaacctca tcattaatgt agtcctaatt ttttatgct                           1359
```